United States Patent
Shang et al.

(10) Patent No.: US 11,960,571 B2
(45) Date of Patent: Apr. 16, 2024

(54) METHOD AND APPARATUS FOR TRAINING IMAGE RECOGNITION MODEL, AND IMAGE RECOGNITION METHOD AND APPARATUS

(71) Applicant: TENCENT TECHNOLOGY (SHENZHEN) COMPANY LIMITED, Shenzhen (CN)

(72) Inventors: Hong Shang, Shenzhen (CN); Han Zheng, Shenzhen (CN); Zhongqian Sun, Shenzhen (CN)

(73) Assignee: TENCENT TECHNOLOGY (SHENZHEN) COMPANY LIMITED, Shenzhen (CN)

(*) Notice: Subject to any disclaimer, the term of this patent is extended or adjusted under 35 U.S.C. 154(b) by 355 days.

(21) Appl. No.: 17/515,312

(22) Filed: Oct. 29, 2021

(65) Prior Publication Data
US 2022/0051059 A1    Feb. 17, 2022

Related U.S. Application Data

(63) Continuation of application No. PCT/CN2020/116998, filed on Sep. 23, 2020.

(30) Foreign Application Priority Data

Oct. 17, 2019    (CN) .......................... 201910989262.8

(51) Int. Cl.
*G06K 9/00*    (2022.01)
*G06F 18/21*    (2023.01)
(Continued)

(52) U.S. Cl.
CPC ........ *G06F 18/2155* (2023.01); *G06F 18/217* (2023.01); *G06N 7/01* (2023.01);
(Continued)

(58) Field of Classification Search
CPC ............ G06N 3/045; G06N 3/08; G06N 3/04; G06N 3/084; G06N 3/044; G06N 3/047;
(Continued)

(56) References Cited

U.S. PATENT DOCUMENTS

2015/0119721 A1    4/2015 Pedersen et al.
2019/0197358 A1*   6/2019 Madani .................. G06N 3/045
(Continued)

FOREIGN PATENT DOCUMENTS

CN        107122375 A    9/2017
CN        108830300 A    11/2018
(Continued)

OTHER PUBLICATIONS

Wu, Mutual consistency learning for semi-supervised medical image segmentation, Medical Image Analysis, Oct. 2022 (Year: 2022).*
(Continued)

*Primary Examiner* — Alex Kok S Liew
(74) *Attorney, Agent, or Firm* — ANOVA LAW GROUP PLLC

(57) ABSTRACT

A method for training an image recognition model includes: obtaining training image sets; obtaining a first predicted probability, a second predicted probability, a third predicted probability, and a fourth predicted probability based on the training image sets by using an initial image recognition model; determining a target loss function according to the first predicted probability, the second predicted probability, the third predicted probability, and the fourth predicted probability; and training the initial image recognition model based on the target loss function, to obtain an image recognition model.

20 Claims, 7 Drawing Sheets

(51) Int. Cl.
*G06F 18/214* (2023.01)
*G06N 7/01* (2023.01)
*G16H 30/40* (2018.01)
*G16H 50/20* (2018.01)

(52) U.S. Cl.
CPC ............. *G16H 30/40* (2018.01); *G16H 50/20* (2018.01); *G06V 2201/03* (2022.01)

(58) Field of Classification Search
CPC ........ G06N 3/048; G06N 3/082; G06N 20/00; G06N 3/063; G06N 3/088; G06N 7/01; G06N 20/10; G06N 20/20; G06N 3/042; G06N 3/09; G06N 5/022; G06N 5/041; G06N 3/006; G06N 3/0675; G06N 5/01; G06N 5/02; G06N 7/023; G06V 10/82; G06V 10/764; G06V 20/41; G06V 20/46; G06V 40/15; G06V 40/161; G06V 40/169; G06V 40/40
See application file for complete search history.

(56) References Cited

U.S. PATENT DOCUMENTS

| | | | |
|---|---|---|---|
| 2020/0110982 A1* | 4/2020 | Gou | ........................ G06N 3/088 |
| 2021/0042580 A1 | 2/2021 | Chen et al. | |
| 2021/0272681 A1 | 9/2021 | Zheng et al. | |

FOREIGN PATENT DOCUMENTS

| | | |
|---|---|---|
| CN | 108986067 A | 12/2018 |
| CN | 109447065 A | 3/2019 |
| CN | 109949309 A | 6/2019 |
| CN | 110009623 A | 7/2019 |
| CN | 110163234 A | 8/2019 |
| CN | 110276741 A | 9/2019 |
| CN | 110738263 A | 1/2020 |
| CN | 110909780 A | 3/2020 |
| WO | 2015066297 A1 | 5/2015 |

OTHER PUBLICATIONS

Zhou, SSMD: Semi-Supervised medical image detection with adaptive consistency and heterogeneous perturbation, Medical Image Analysis, vol. 72, Aug. 2021 (Year: 2021).*
The State Intellectual Property Office of the People's Republic of China (SIPO) Office Action 1 for for 201910989262.8 dated Sep. 8, 2020 8 Pages (including translation).
The World Intellectual Property Organization (WIPO) International Search Report for PCT/CN2020/116998 dated Dec. 31, 2020 5 Pages (including translation).
Jia Wu et al., "Application of Convolutional Neural Network Considering Regional Information in Image Semantic Segmentation," Science Technology and Engineering, vol. 18 No. 21, Jul. 31, 2018 (Jul. 31, 2018). 7 pages.
R. Caruana, "Multitask learning," Machine learning 28(1), pp. 41-75, 1997. 35 pages.
Z. Zhang et al., "Facial landmark detection by deep multi-task learning," In: European Conference on Computer Vision, pp. 94-108, Springer, 2014. 15 pages.
S. Ruder, "An overview of multi-task learning in deep neural networks," arXiv:1706.05098, Jun. 15, 2017. 14 pages.
M. Sajjadi et al., "Regularization with stochastic transformations and perturbations for deep semi-supervised learning," NIPS 2016. 9 pages.
S. Laine et al., "Temporal ensembling for semi-supervised learning." arXiv:1610.02242, Mar. 15, 2016. 13 pages.
T. Miyato et al., "Virtual adversarial training: a regularization method for supervised and semi-supervised learning," IEEE transactions on pattern analysis and machine intelligence, 2018. 16 pages.
The European Patent Office (EPO) The Extended European Search Report for 20877797.9 dated Jul. 14, 2022 10 pages.
Seung Yeon Shin et al., "Joint Weakly and Semi-Supervised Deep Learning for Localization and Classification of Masses in Breast Ultrasound Images," arXiv:1710.03778v1, Oct. 10, 2017 (Oct. 10, 2017). 9 pages.
Yutong Xie et al., "Semi- and Weakly Supervised Directional Bootstrapping Model for Automated Skin Lesion Segmentation," arXiv:1903.03313v1, Mar. 8, 2019 (Mar. 8, 2019). 8 pages.

* cited by examiner

METHOD AND APPARATUS FOR TRAINING IMAGE RECOGNITION MODEL, AND IMAGE RECOGNITION METHOD AND APPARATUS

CROSS-REFERENCES TO RELATED APPLICATIONS

This application is a continuation application of PCT Patent Application No. PCT/CN2020/116998, filed on Sep. 23, 2020, which claims priority to Chinese Patent Application No. 2019109892628, entitled "METHOD AND APPARATUS FOR TRAINING IMAGE RECOGNITION MODEL, AND IMAGE RECOGNITION METHOD AND APPARATUS" filed with the China National Intellectual Property Administration on Oct. 17, 2019, the entire contents of both of which are incorporated herein by reference.

FIELD OF THE TECHNOLOGY

The present disclosure relates to the field of artificial intelligence (AI), and in particular, to an image processing technology.

BACKGROUND OF THE DISCLOSURE

As population continuously increases, burden on medical systems is increasing, and a requirement for medical resources is also increasing. In an actual application, medical staff may analyze an illness of a patient by using a medical image. To help the medical staff diagnose the illness more quickly and more accurately, and the medical image may be recognized by using an automatic diagnostic device.

Currently, to implement automatic diagnosis, a large quantity of medical images are often required to train an image recognition model. The medical images need to be labeled by the medical staff, that is, the medical staff can make a judgment on each medical image according to clinical experience. For example, whether a disease exists in the medical image or not, and a position of a lesion in the medical image.

However, as the quantity of medical images is continuously accumulated, the complexity of the lesion is increasingly high, labeling becomes increasingly difficult, and labeling resources that can be used for training the image recognition model are limited. Moreover, the limited labeling resources results in that only a small part of marked medical images can be used in a model training process. In addition, because model training usually needs to be implemented in combination with a specific task, and for different tasks, a training set corresponding to a task needs to be adopted. As a result, the labeled medical image cannot be effectively used and data of a training set of some tasks is insufficient, resulting in relatively low accuracy of a model prediction effect.

SUMMARY

The embodiments of the present disclosure provide a method and an apparatus for training an image recognition model and an image recognition method and apparatus, which can train a model by using a labeled medical image for different tasks and an unlabeled medical image together. The labeled image and the unlabeled image are effectively used, so that a requirement for image labeling is reduced and a data volume for training is increased, thereby improving a model prediction effect while saving labeling resources.

In view of this, one aspect of the present disclosure provides a method for training an image recognition model. The method includes: obtaining training image sets; obtaining a first predicted probability, a second predicted probability, a third predicted probability, and a fourth predicted probability based on the training image sets by using an initial image recognition model; determining a target loss function according to the first predicted probability, the second predicted probability, the third predicted probability, and the fourth predicted probability; and training the initial image recognition model based on the target loss function, to obtain an image recognition model. The training image sets includes at least a first image set, a second image set, and a third image set, the first image set includes at least one first image, the second image set includes at least one second image and at least one perturbed image, and the third image set includes at least one third image, the first image being a labeled image corresponding to a first task, the second image being an unlabeled image corresponding to the first task, the third image being a labeled image corresponding to a second task, the first task and the second task being different tasks. The first predicted probability is a predicted result outputted based on the first image set, the second predicted probability and the third predicted probability are predicted results outputted based on the second image set, and the fourth predicted probability is a predicted result outputted based on the third image set. The target loss function includes at least a first loss function determined according to the first predicted probability, a second loss function determined according to the second predicted probability and the third predicted probability, and a third loss function determined according to the fourth predicted probability.

Another second aspect of the present disclosure provides an image recognition method, including: obtaining an image to be recognized; obtaining an image recognition result corresponding to the to-be-recognized image by using an image recognition model, the image recognition model being the image recognition model trained according to the foregoing method; and displaying the image recognition result.

Another aspect of the present disclosure provides an apparatus for training an image recognition model, including: an obtaining module, configured to obtain training image sets, the training image sets including at least a first image set, a second image set, and a third image set, the first image set including at least one first image, the second image set including at least one second image and at least one perturbed image, the third image set including at least one third image, the first image being a labeled image corresponding to a first task, the second image being an unlabeled image corresponding to the first task, the third image being a labeled image corresponding to a second task, the first task and the second task being different tasks; the obtaining module, further configured to obtain a first predicted probability, a second predicted probability, a third predicted probability, and a fourth predicted probability based on the training image sets by using an initial image recognition model, the first predicted probability being a predicted result outputted based on the first image set, the second predicted probability and the third predicted probability being predicted results outputted based on the second image set, and the fourth predicted probability being a predicted result outputted based on the third image set; a determining module, configured to determine a target loss function according to the first predicted probability, the second predicted probability, the third predicted probability, and the fourth predicted probability, the target loss function including at least a first loss function determined according to the first predicted probability, a second loss function determined according to the second predicted probability and the third predicted probability, and a third loss function determined according to the fourth predicted probability; and a training module, configured to train the initial image recognition model according to the target loss function determined by the determining module, to obtain an image recognition model.

Another aspect of the present disclosure provides an electronic device, including: a memory, a transceiver, a processor, and a bus system, the memory being configured to store a program; the processor being configured to execute the program in the memory, to perform: obtaining training image sets; obtaining a first predicted probability, a second predicted probability, a third predicted probability, and a fourth predicted probability based on the training image sets by using an initial image recognition model; determining a target loss function according to the first predicted probability, the second predicted probability, the third predicted probability, and the fourth predicted probability; and training the initial image recognition model based on the target loss function, to obtain an image recognition model. The training image sets includes at least a first image set, a second image set, and a third image set, the first image set includes at least one first image, the second image set includes at least one second image and at least one perturbed image, and the third image set includes at least one third image, the first image being a labeled image corresponding to a first task, the second image being an unlabeled image corresponding to the first task, the third image being a labeled image corresponding to a second task, the first task and the second task being different tasks. The first predicted probability is a predicted result outputted based on the first image set, the second predicted probability and the third predicted probability are predicted results outputted based on the second image set, and the fourth predicted probability is a predicted result outputted based on the third image set. The target loss function includes at least a first loss function determined according to the first predicted probability, a second loss function determined according to the second predicted probability and the third predicted probability, and a third loss function determined according to the fourth predicted probability. The bus system is configured to connect the memory and the processor to enable communication between the memory and the processor.

Another aspect of the present disclosure provides an endoscope medical diagnosis system, including: a probe, a circuit, a processor, and a display, the circuit being configured to excite the probe to obtain a to-be-recognized image; the processor being configured to obtain an image recognition result corresponding to the to-be-recognized image by using an image recognition model, the image recognition model being the image recognition model trained according to the foregoing method; and the display being configured to display the image recognition result.

Another aspect of the present disclosure provides a non-transitory computer-readable storage medium, storing instructions, the instructions, when run on a computer, causing the computer to perform: obtaining training image sets; obtaining a first predicted probability, a second predicted probability, a third predicted probability, and a fourth predicted probability based on the training image sets by using an initial image recognition model; determining a target loss function according to the first predicted probability, the second predicted probability, the third predicted probability, and the fourth predicted probability; and training the initial image recognition model based on the target loss function, to obtain an image recognition model. The training image sets includes at least a first image set, a second image set, and a third image set, the first image set includes at least one first image, the second image set includes at least one second image and at least one perturbed image, and the third image set includes at least one third image, the first image being a labeled image corresponding to a first task, the second image being an unlabeled image corresponding to the first task, the third image being a labeled image corresponding to a second task, the first task and the second task being different tasks. The first predicted probability is a predicted result outputted based on the first image set, the second predicted probability and the third predicted probability are predicted results outputted based on the second image set, and the fourth predicted probability is a predicted result outputted based on the third image set. The target loss function includes at least a first loss function determined according to the first predicted probability, a second loss function determined according to the second predicted probability and the third predicted probability, and a third loss function determined according to the fourth predicted probability.

It can be seen from the foregoing technical solutions that the embodiments of the present disclosure have the following advantages:

The embodiments of the present disclosure provide a method for training an image recognition model. Training image sets are obtained first, then a first predicted probability, a second predicted probability, a third predicted probability, and a fourth predicted probability are obtained based on the training image sets by using an initial image recognition model, subsequently, a target loss function is determined according to the first predicted probability, the second predicted probability, the third predicted probability, and the fourth predicted probability, and finally the initial image recognition model is trained based on the target loss function, to obtain an image recognition model. In this way, a model can be trained by using a labeled medical image for different tasks and an unlabeled medical image together. The labeled image and the unlabeled image are effectively used, so that a requirement for image labeling is reduced and a data volume for training is increased, thereby improving a model prediction effect while saving labeling resources.

DESCRIPTION OF EMBODIMENTS

The embodiments of the present disclosure provide a method and an apparatus for training an image recognition model and an image recognition method and apparatus, a model is trained by using a labeled medical image for different tasks and an unlabeled medical image together, and the labeled image and the unlabeled image are effectively used, so that a requirement for image labeling is reduced and a data volume for training is increased, thereby improving a model prediction effect while saving labeling resources.

It is to be understood that the method for training an image recognition model and the image recognition method provided by the present disclosure are applicable to the medical field of artificial intelligence (AI), and are particularly applicable to the field of medical image recognition based on a computer vision (CV) technology.

The most common medical images in the medical field include, but are not limited to, an endoscope image, an angiography image, an angiocardiographic image, a computerized tomography (CT) image, a B-mode ultrasound image, and a pathology image. Because the medical image can directly reflect a lesion occurring inside a tissue, and is an important basis for a doctor to perform disease diagnosis, and even a final basis of diagnosis of some diseases. For example, in diagnosis of cancer, a cancer diagnosis result is determined by observing a radiographic image of a lesion, which includes observing whether there is a shadow, a plaque, or vasodilation. In the present disclosure, an endoscope image may be recognized, and is applied to automatic diagnosis of an endoscope image to assist a doctor in improving diagnosis efficiency and accuracy, and on this basis, available data of another form is further used to assist model training to improve model accuracy.

The medical image is an important information entry for the doctor to learn an illness of a patient. Although a current high-quality medical imaging device has become popular, accurate interpretation of the medical image often requires the doctor to have professional knowledge background and long-term experience accumulation. Considering that population is large, burden on a medical system is heavy, and a quantity of experienced doctors is insufficient and is mainly concentrated in large-scale grade-A tertiary hospitals in first-tier cities, resulting in scarcity of medical resources. According to the method provided by the present disclosure, based on labeled data of a target task, unlabeled data (that is, semi-supervised learning) of the target task and labeled data (that is, multi-task learning, MTL) of another related task can be further used, and information in existing data of various types is maximized to assist the model training, to improve a model effect.

Figure 1:
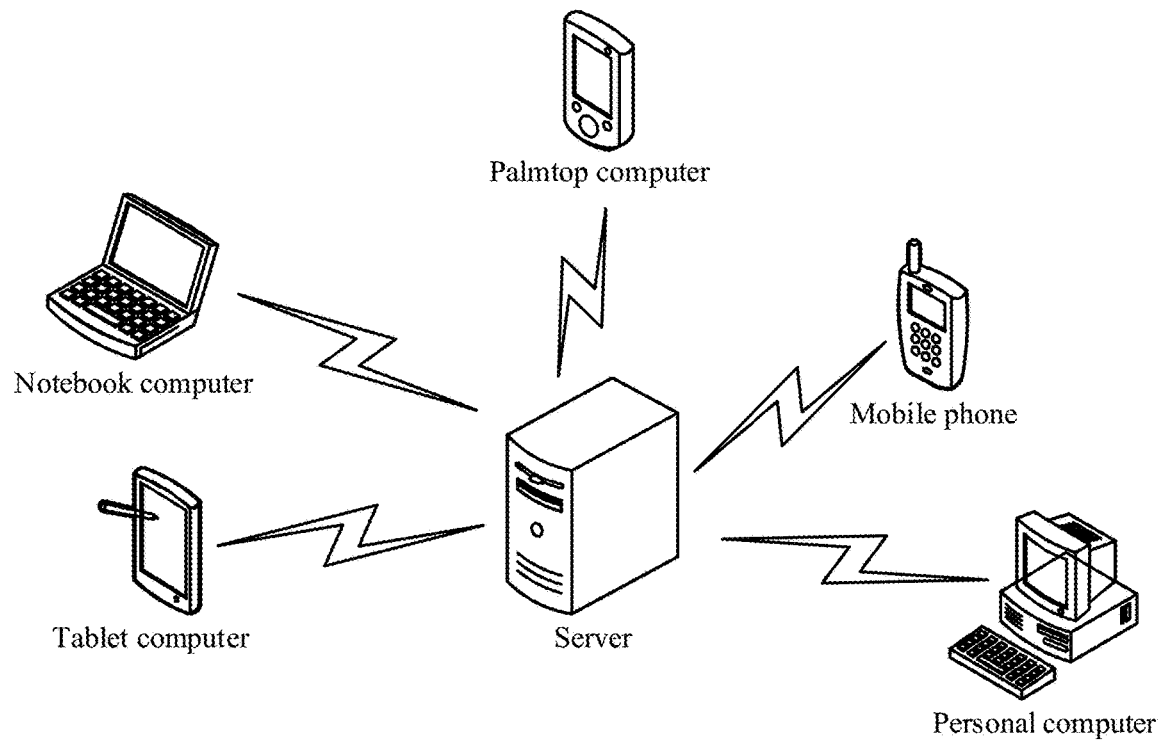
FIG. 1 is a schematic architectural diagram of an image recognition system according to an embodiment of the present disclosure.

For ease of understanding, the present disclosure provides an image recognition method, and the method is applicable to an image recognition system shown in FIG. 1. FIG. 1 is a schematic architectural diagram of an image recognition system according to an embodiment of the present disclosure. As shown in the figure, the image recognition system may include a medical device, and the medical device may be specifically an endoscope device, an electron microscope, or the like. After acquiring a to-be-recognized medical image, the medical device may recognize the medical image according to a task type by using a trained image recognition model. Automatic diagnosis of an endoscope image is used as an example, recognition may be performed according to different parts (for example, esophagus, stomach, duodenum, and colorectum), or recognition may be performed according to different target tasks (for example, distinguishing benign or malignant, distinguishing parts, or distinguishing whether a picture is qualified), and a visualization result may be obtained finally, to provide a doctor with a focus region.

Optionally, after acquiring the to-be-recognized medical image, the medical device may send the medical image to a terminal device, the terminal device may recognize the medical image by using the trained image recognition model, to obtain the visualization result for providing a doctor with a focus region and displaying the result on an interface.

Optionally, after acquiring the to-be-recognized medical image, the medical device may send the medical image to a server, and the server recognizes the medical image by using the trained image recognition model. After obtaining a recognition result, the server may feed the result back to the terminal device or the medical device, and the terminal device or the medical device performs displaying.

The terminal device includes, but is not limited to, a tablet computer, a notebook computer, a palmtop computer, a mobile phone, a speech interaction device, and a personal computer (PC), and is not limited herein.

Figure 2:
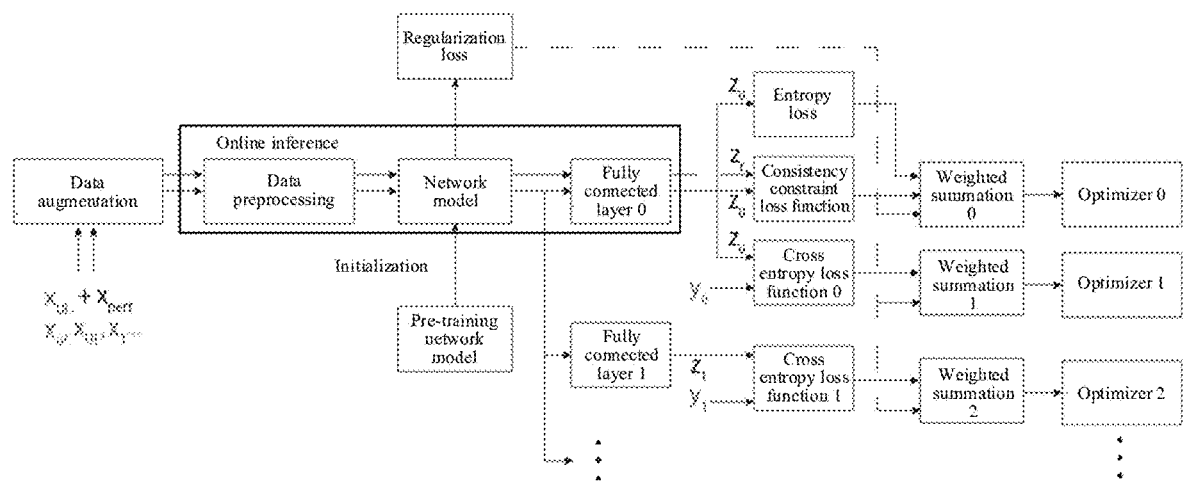
FIG. 2 is an entire schematic structural diagram of training an image recognition model according to an embodiment of the present disclosure.

The image recognition model used in the present disclosure may be trained by using an architecture shown in FIG. 2. FIG. 2 is an entire schematic structural diagram of training an image recognition model according to an embodiment of the present disclosure. As shown in the figure, the image recognition model in the present disclosure may adopt a deep learning model structure, for example, a residual network (ResNet) structure or a dense convolutional network structure. During training, data augmentation and data preprocessing may be performed on training data, and an end-to-end method based stochastic gradient descent is adopted for training. Alternate training of each task may be selected. For alternate training, labeled data of a target task, auxiliary task data in the MTL, and unlabeled data in the semi-supervised learning are inputted sequentially, a corresponding optimizer is invoked to reduce a corresponding loss value, so as to update parameters of an overlapped part and unique parameters of the target task. Hybrid training may be alternatively selected. For hybrid training, that is, the labeled data of the target task, the auxiliary task data in the MTL, and the unlabeled data in the semi-supervised learning that are mixed are inputted each time, an optimizer is invoked after corresponding loss values are added, thereby reducing a total loss value.

After an image recognition model is obtained through training, an online inference part shown in FIG. 2 may be used for prediction, and the online inference part includes data preprocessing, a network model, and a fully connected layer. In an actual application, the online inference part may further include another network layer. This is merely an example and is not to be understood as a limitation on the present disclosure.

Figure 3:
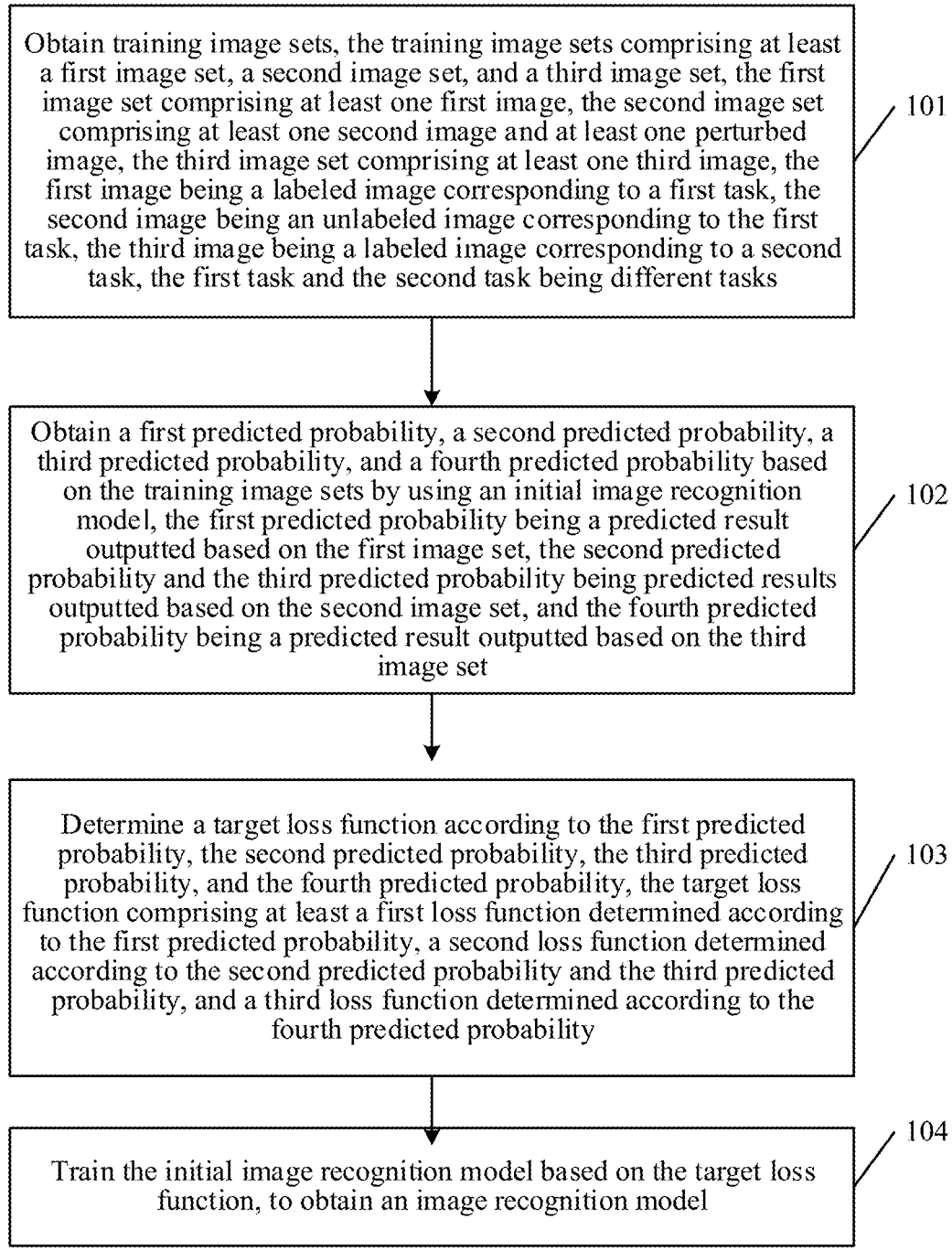
FIG. 3 is a schematic diagram of an embodiment of a method for training an image recognition model according to an embodiment of the present disclosure.

Referring to FIG. 3, an embodiment of a method for training an image recognition model in this embodiment of the present disclosure includes the following steps:

101. Obtain training image sets, the training image sets including at least a first image set, a second image set, and a third image set, the first image set including at least one first image, the second image set including at least one second image and at least one perturbed image, the third image set including at least one third image, the first image being a labeled image corresponding to a first task, the second image being an unlabeled image corresponding to the first task, the third image being a labeled image corresponding to a second task, the first task and the second task being different tasks.

In some embodiments, an apparatus for training an image recognition model obtains training image sets. It may be understood that the apparatus for training an image recognition model may be deployed on the terminal device or may be deployed on the server. Because a data volume for training is usually relatively large, model training may be performed by using the server. However, this is not to be understood as a limitation of the present disclosure.

The training image sets include at least a first image set, a second image set, and a third image set, and each of the first image set, the second image set, and the third image set belongs to a training sample. The first image set includes at least one first image (which may be represented as $x_0$), the second image set includes at least one second image (which may be represented as $x_{UL}$) and at least one perturbed image (which may be represented as $x_{pert}$), and the third image set includes at least one third image (which may be represented as $x_1$). The first image is a labeled image that carries labeled information and corresponds to a first task, the second image is an unlabeled image that does not carry the labeled information and corresponds to the first task, and the third image is a labeled image that carries the labeled information and corresponds to a second task. The first task and the second task are different tasks. The perturbed image is obtained by performing random scrambling on the second image, and a size of the perturbed image is usually the same as a size of the second image. The random scrambling includes, but is not limited to, flipping, rotation, and translation. It may be understood that two times of random scrambling may be performed on one second image, that is, one second image may correspond to two perturbed images. In addition, the perturbed image is usually generated during training.

102. Obtain a first predicted probability, a second predicted probability, a third predicted probability, and a fourth predicted probability based on the training image sets by using an initial image recognition model, the first predicted probability being a predicted result outputted based on the first image set, the second predicted probability and the third predicted probability being predicted results outputted based on the second image set, and the fourth predicted probability being a predicted result outputted based on the third image set. The initial image recognition model is considered as an image recognition model to be trained.

In some embodiments, two training processes, which are respectively semi-supervised learning and multi-task learning (MTL), are adopted. The first image set and the second image set are used for the semi-supervised learning, the second predicted probability and the third predicted probability are output results of the semi-supervised learning, the third image set is used for the MTL, and the fourth predicted probability is an output result of the MTL.

The semi-supervised learning assists training by using unlabeled data of the same task to improve a model effect. The significance of labeling is to determine whether a result of prediction of a current model is correct, so as to server as an indication for evaluating quality of the mode. That is, a target loss function is set, a more accurate current to-be-trained image recognition model indicates a smaller value of the target loss function, and a model training process is an optimization process of causing the target loss function to obtain a minimum value. For labeled image data, quality of a model may be evaluated by using a cross entropy loss function. However, for unlabeled image data, the quality of the model cannot be evaluated by using a label. Therefore, the same picture may be inputted into a network after two times of random disturbance, and a difference between two prediction results is determined by using a consistency constraint loss function. The model training is to reduce the different between the two prediction results.

The MTL assists training by using a labeled data set in another related task, to improve the model effect. In a conventional machine learning method, a model is independently trained for each task, but in an MTL method, a plurality of related tasks may be trained at the same time by using one network model. Some parameters of the network model are shared by the tasks, and some other parameters of the network model are unique to each task.

103. Determine a target loss function according to the first predicted probability, the second predicted probability, the third predicted probability, and the fourth predicted probability, the target loss function including at least a first loss function, a second loss function, and a third loss function, the first loss function being determined according to the first predicted probability, the second loss function being determined according to the second predicted probability and the third predicted probability, and the third loss function being determined according to the fourth predicted probability.

In some embodiments, the apparatus for training an image recognition model determines a first loss function according to the first predicted probability and labeled information corresponding to the first image set, the first predicted probability being a predicted value, and the labeled information corresponding to the first image set being a real value, and calculates the first loss function based on the predicted value and the real value. The apparatus for training an image recognition model determines a second loss function according to the second predicted probability and the third predicted probability, both the second predicted probability and the third predicted probability being predicted values. The apparatus for training an image recognition model determines a third loss function according to the fourth predicted probability and labeled information corresponding to the third image set, the fourth predicted probability being a predicted value, and the labeled information corresponding to the third image set being a real value, and calculates the third loss function based on the predicted value and the real value. A target loss function may be obtained according to the first loss function, the second loss function, and the third loss function.

104. Train the initial image recognition model based on the target loss function, to obtain an image recognition model.

In some embodiments, when the target loss function converges, it indicates that training of the initial image recognition model is completed. In this case, the initial image recognition model is an image recognition model. It may be understood that in an actual application, it may be also considered that the target loss function has converged when a quantity of times of training reaches a threshold.

The embodiments of the present disclosure provide a method for training an image recognition model. Training image sets are obtained first, then a first predicted probability, a second predicted probability, a third predicted probability, and a fourth predicted probability are obtained based on the training image sets by using an initial image recognition model, subsequently, a target loss function is determined according to the first predicted probability, the second predicted probability, the third predicted probability, and the fourth predicted probability, and finally the initial image recognition model is trained based on the target loss function, to obtain an image recognition model. In this way, a model can be trained by using a labeled medical image for different tasks and an unlabeled medical image together. The labeled image and the unlabeled image are effectively used, so that a requirement for image labeling is reduced and a data volume for training is increased, thereby improving a model prediction effect while saving labeling resources.

Optionally, based on the embodiment corresponding to FIG. 3, in a first optional embodiment of the method for training an image recognition model according to the embodiments of the present disclosure, the obtaining a first predicted probability, a second predicted probability, a third predicted probability, and a fourth predicted probability based on the training image sets by using an initial image recognition model may include:

obtaining the first predicted probability based on the first image set by using the initial image recognition model;

obtaining the second predicted probability and the third predicted probability based on the second image set by using the initial image recognition model; and obtaining the fourth predicted probability based on the third image set by using the initial image recognition model.

In some embodiments, the apparatus for training an image recognition model inputs a second image set into the initial image recognition model. Specifically, the second image set includes a second image and a perturbed image. It is assumed that first random scrambling is performed on a second image A to obtain a perturbed image A, and second random scrambling is performed on the second image A to obtain a perturbed image B. Therefore, the apparatus for training an image recognition model first inputs the second image A and the perturbed image A into the initial image recognition model, and the initial image recognition model outputs a second predicted probability. Subsequently, the apparatus for training an image recognition model inputs the second image A and the perturbed image B into the initial image recognition model, the initial image recognition model outputs a third predicted probability, and two predicted probabilities are obtained respectively through two predictions. In an actual application, two times of random scrambling may be performed on each second image.

Figure 4:
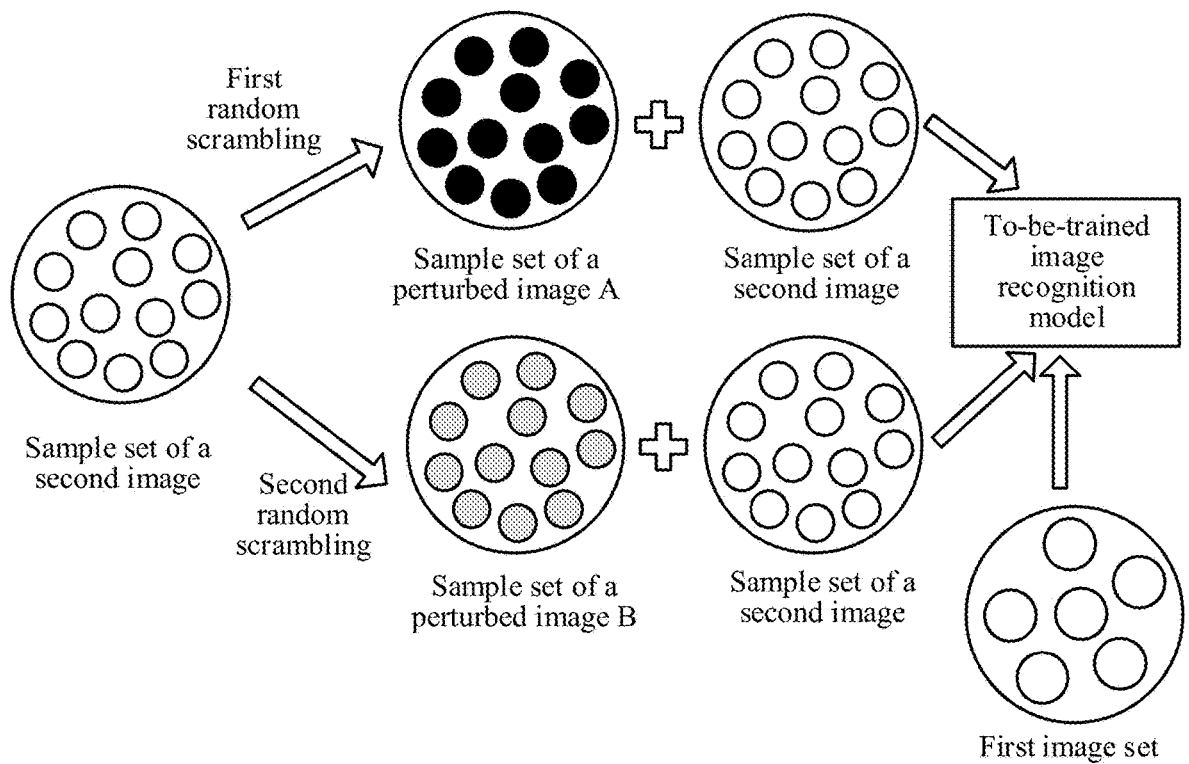
FIG. 4 is a schematic diagram of an embodiment based on semi-supervised learning according to an embodiment of the present disclosure.

For ease of understanding, FIG. 4 is a schematic diagram of an embodiment of performing training based on an unlabeled sample according to an embodiment of the present disclosure. As shown in the figure, a sample set of the second image includes at least one second image. First random scrambling is first performed on each second image in the sample set of the second image, to obtain a sample set of the perturbed image A. Subsequently, second random scrambling is performed on each second image in the sample set of the second image, to obtain a sample set of the perturbed image B. Both the sample set of the second image and the sample set of the perturbed image A are inputted into the initial image recognition model, to obtain a first predicted probability corresponding to each sample. Both the sample set of the second image and the sample set of the perturbed image B are inputted into the initial image recognition model, to obtain a second predicted probability corresponding to each sample.

In some embodiments, the apparatus for training an image recognition model further inputs a first image set into the initial image recognition model. Specifically, the first image set includes a first image, and the first image is a labeled image. Similarly, the apparatus for training an image recognition model further inputs a third image set into the initial image recognition model. Specifically, the third image set includes a third image, and the third image is similar to the first image and is also a labeled image. The difference is that the first image set in which the first image is located and the third image set in which the third image is located correspond to different learning tasks. For example, the first image set is labeled for a lesion positioning task, that is, content labeled in the first image is a position of a lesion, for example, the lesion is in the esophagus, stomach, duodenum, colorectum, or the like. However, the third image set is labeled for a tumor property task, that is, content labeled in the third image is a tumor property such as a malignant tumor or a benign tumor. It may be understood that in an actual application, other different tasks may be further set according to a requirement. This is merely an example and is not to be understood as a limitation on the present disclosure.

Figure 5:
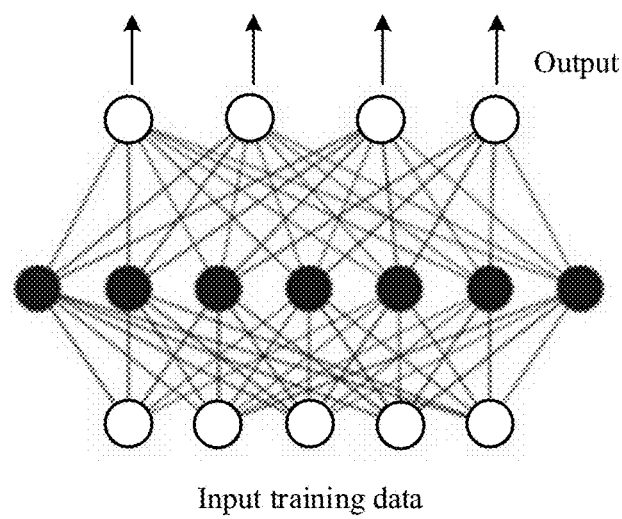
FIG. 5 is a schematic diagram of an embodiment based on multi-task learning according to an embodiment of the present disclosure.

For ease of description, FIG. 5 is a schematic diagram of an embodiment based on MTL according to an embodiment of the present disclosure. As shown in the figure, the MTL assists training by using another related labeled data set, to improve a model effect. In a conventional machine learning method, a model is independently trained for each task, but in an MTL method, a plurality of related tasks may be trained at the same time by using one network model. Some parameters of the network model are shared by the tasks, and some other parameters of the network model are unique to each task. As shown in FIG. 5, for inputted training data, prediction results under four different tasks are outputted by using the initial image recognition model, parameters are shared among different tasks, and all data sets of all tasks are used, so that a data volume for training is increased.

The MTL has a plurality of forms, including, but is not limited to, joint learning, learning to learn, and learning with an auxiliary task. Generally, optimizing a plurality of loss functions is equivalent to performing the MTL. Even if only one loss function is optimized, an original task model may be improved by using an auxiliary task. The MTL provided in the present disclosure may be implemented based on parameter hard sharing, or may be implemented based on parameter soft sharing. The parameter hard sharing is typically implemented by sharing a hidden layer between all tasks while preserving output layers of several specific tasks. In the parameter soft sharing, each task has a separate model, and each model includes a respective parameter.

Secondly, in this embodiment of the present disclosure, a method for obtaining the first predicted probability, the second predicted probability, the third predicted probability, and the fourth predicted probability is provided. The second predicted probability and the third predicted probability are obtained based on the second image set by using the semi-supervised learning, and the fourth predicted probability is obtained based on the third image set by using the MTL. In the foregoing manner, training is effectively performed by using unlabeled data, to improve a model effect, and a requirement for labeled data is reduced while a better effect is obtained, thereby reducing product development costs and accelerating a product development cycle. In addition, a plurality of related tasks can be further trained at the same time by using one image recognition model, some parameters of the image recognition model are shared by various tasks, and some other parameters are unique to each task. Shared parameters use all data sets of all tasks, so that a data volume for training is increased, and meanwhile unique noise of each training set is canceled, thereby improving a generalization ability of the model, and reducing overfitting of the model. An independent output layer may select a most relevant feature for a task from a shared part, and learn a unique classification boundary of each task, so that the model has sufficient flexibility, and can obtain relatively high accuracy for an image recognition task.

Optionally, based on the embodiment corresponding to FIG. 3, in a second optional embodiment of the method for training an image recognition model according to the embodiments of the present disclosure, the obtaining the first predicted probability based on the first image set by using the initial image recognition model may include:

obtaining a first predicted value based on the at least one first image by using a fully connected layer included in the initial image recognition model; and performing normalization processing on the first predicted value, to obtain the first predicted probability.

In some embodiments, the method for generating the first predicted probability is described. For ease of description, one first image in the first image set is used as an example for description below. It may be understood that other first images in the first image set are also processed in a similar manner, and details are not described herein again.

Specifically, it is assumed that the first image is represented as $x_0$, and labeled information of the first image is $y_0$. The labeled information is used for representing a classification label under a classification task, for example, the classification task is a lesion positioning task, and the classification label may be different parts. For example, a label 1 represents an esophagus part, a label 2 represents a stomach, a label 3 represents a duodenal part, a label 4 represents a colorectal part, and a label 5 represents no type. In another example, the classification task is a task of distinguishing tumor properties, and the classification label may be different degrees of tumor progression. For example, a label 1 represents a benign tumor, a label 2 represents a malignant tumor, and a label 3 represents no tumor. In another example, the classification task is a task of distinguishing qualified conditions of a picture, and the classification label may be different picture qualification conditions. For example, a label 1 represents that the picture is qualified, and a label 2 represents that the picture is not qualified.

A first predicted value is outputted after the first image $x_0$ belonging to a second task passes through a fully connected (FC) layer, the first predicted value being represented as $z_0$ and the first predicted probability $p_0$ of the first image is obtained after the first predicted value $z_0$ passes through a softmax layer, that is, normalization processing is implemented. The first predicted probability is obtained through calculation in the following manner:

$$p_0[i] = \frac{e^{z_0[i]}}{\sum_{k=0}^{C-1} e^{z_0[k]}};$$

where $p_0$ represents the first predicted probability, $p_0[i]$ represents an $i^{th}$ unit in the first predicted probability, C represents a total quantity of types, k represents a $k^{th}$ type, and a value of t is an integer greater than or equal to 0 and less than or equal to C−1.

The last layer of the initial image recognition model may be the FC layer+the softmax layer. The FC layer multiplies a weight matrix and an input vector and then adds a bias, and maps N real numbers into K fractions, and the softmax layer maps K real numbers into K probabilities within a range (0, 1) and ensures that a sum of the K real numbers is 1.

Secondly, in this embodiment of the present disclosure, the method for generating the first predicted probability is provided, that is, first, a first predicted value of the first image is obtained by using an FC layer included in the initial image recognition model, and then normalization processing is performed on the first predicted value of the first image, to obtain the first predicted probability of the first image. In the foregoing manner, after normalization processing is performed on a predicted value, a prediction class of a sample can be reflected more intuitively, thereby improving the accuracy of training sample classification and improving the model training efficiency and accuracy.

Optionally, based on the embodiment corresponding to FIG. 3, in a third optional embodiment of the method for training an image recognition model according to the embodiments of the present disclosure, the obtaining the second predicted probability and the third predicted probability based on the second image set by using the initial image recognition model may include:

generating a first perturbed image set according to the at least one second image, the first perturbed image set including at least one first perturbed image, the first perturbed image having a correspondence with the second image (e.g., each first perturbed image having a corresponding second image), and the first perturbed image being the perturbed image;

generating a second perturbed image set according to the at least one second image, the second perturbed image set including at least one second perturbed image, the second perturbed image having a correspondence with the second image (e.g., each second perturbed image having a corresponding second image), and the second perturbed image being perturbed image;

obtaining the second predicted probability based on the at least one second image and the first perturbed image set by using the initial image recognition model; and obtaining the third predicted probability based on the at least one second image and the second perturbed image set by using the initial image recognition model.

In some embodiments, a data processing manner based on semi-supervised learning is described. First, the apparatus for training an image recognition model obtains at least one second image, the second image herein being an unlabeled image. Subsequently, two times of random scrambling are performed on each second image, and a first perturbed image set is obtained after first random scrambling, the first perturbed image set including at least one first perturbed image, that is, each first perturbed image corresponds to a second image. Similarly, a second perturbed image set is obtained after second random scrambling, the second perturbed image set including at least one second perturbed image, that is, each second perturbed image corresponds to a second image, and a quantity of second perturbed images being usually the same as a quantity of first perturbed images. The at least one second image and the first perturbed image set are inputted into the initial image recognition model, to obtain the second predicted probability. For example, 1000 second images and 1000 first perturbed images may be inputted into the initial image recognition model, or 100 second images and 100 first perturbed images may be inputted into the initial image recognition model. A quantity of second images is not limited this time. Similarly, the at least one second image and the second perturbed image set are inputted into the initial image recognition model, to obtain the third predicted probability. The second predicted probability may be the same as or different from the third predicted probability.

It may be understood that in an actual application, a result outputted by the initial image recognition model may be a predicted value, and a predicted probability may be obtained after normalization processing is performed on the predicted value.

Data augmentation needs to be performed on the second image during random scrambling, and in addition to performing flipping, rotation, and translation on the second image, a direction, a position, a proportion, a brightness, or the like of the second image may be changed. A random factor such as a random dropout may be added to the initial image recognition model. The dropout is a method for optimizing an artificial neural network with a depth structure, and some weights or outputs of a hidden layer are return to zero randomly during learning, to reduce interdependence between nodes, thereby achieving regularization of a neural network. If a perturbed image is random noise, a random scrambling process may be referred to as a Pi-model. If the perturbed image is adversarial perturbation, the random scrambling process may be referred to as virtual adversarial training (VAT).

Secondly, in this embodiment of the present disclosure, the data processing manner based on semi-supervised learning is provided, that is, two times of random scrambling are performed on a second image, to obtain a first perturbed image and a second perturbed image, and then the second image and each of the first perturbed image and the second perturbed image form two training samples to be inputted into a model, to obtain two predicted probabilities. In the foregoing manner, random scrambling is performed on an unlabeled image, to obtain images with different perturbation degrees as samples for model training, and manual intervention is not required during random scrambling, thereby improving the model training efficiency. In addition, randomized processing can improve the generalization ability of the model, thereby improving a model training effect. The semi-supervised learning avoids waste of data and resources, and resolves problems that a generalization ability of a model of full supervised learning is not strong and a model of unsupervised learning is inaccurate.

Optionally, based on the embodiment corresponding to FIG. 3, in a fourth optional embodiment of the method for training an image recognition model according to the embodiments of the present disclosure, the obtaining the fourth predicted probability based on the third image set by using the initial image recognition model may include:

obtaining a fourth predicted value based on the at least one third image by using an FC layer included in the initial image recognition model; and performing normalization processing on the fourth predicted value, to obtain the fourth predicted probability.

In some embodiments, the method for generating the fourth predicted probability is described. For ease of description, one third image in the third image set is used as an example for description below. It may be understood that other third images in the third image set are also processed in a similar manner, and details are not described herein again.

Specifically, it is assumed that the third image is represented as $x_1$, and labeled information of the third image is $y_1$. The labeled information is used for representing a classification label under a classification task, for example, the classification task is a lesion positioning task, and the classification label may be different parts. For example, a label 1 represents an esophagus part, a label 2 represents a stomach, a label 3 represents a duodenal part, a label 4 represents a colorectal part, and a label 5 represents no type. In another example, the classification task is a task of distinguishing tumor properties, and the classification label may be different degrees of tumor progression. For example, a label 1 represents a benign tumor, a label 2 represents a malignant tumor, and a label 3 represents no tumor. In another example, the classification task is a task of distinguishing qualified conditions of a picture, and the classification label may be different picture qualification conditions. For example, a label 1 represents that the picture is qualified, and a label 2 represents that the picture is not qualified. The labeled information of the third image belongs to the second task, the labeled information of the first image belongs to the first task, and the two tasks are different.

A second predicted value is outputted after the third image $x_1$ belonging to the second task passes through the FC layer, the second predicted value being represented as $z_1$, and the fourth predicted probability $p_1$ of the third image is obtained after the second predicted value $z_1$ passes through the softmax layer, that is, normalization processing is implemented. The fourth predicted probability is obtained through calculation in the following manner:

$$p_1[i] = \frac{e^{z_1[i]}}{\sum_{k=0}^{C-1} e^{z_1[k]}},$$

where $p_1$ represents the fourth predicted probability, $p_1[i]$ represents an $i^{th}$ unit in the fourth predicted probability, C represents a total quantity of types, k represents a $k^{th}$ type, and a value of t is an integer greater than or equal to 0 and less than or equal to C−1.

The last layer of the initial image recognition model may be the FC layer+the softmax layer. The FC layer multiplies a weight matrix and an input vector and then adds a bias, and maps N real numbers into K fractions, and the softmax layer maps K real numbers into K probabilities within a range (0, 1) and ensures that a sum of the K real numbers is 1.

Secondly, in this embodiment of the present disclosure, the method for generating the fourth predicted probability is provided, that is, first, a second predicted value of the third image is obtained by using an FC layer included in the initial image recognition model, and then normalization processing is performed on the second predicted value of the third image, to obtain the fourth predicted probability of the third image. In the foregoing manner, after normalization processing is performed on a predicted value, a prediction class of a sample can be reflected more intuitively, thereby improving the accuracy of training sample classification and improving the model training efficiency and accuracy.

Optionally, based on the embodiment corresponding to FIG. 3, in a fifth optional embodiment of the method for training an image recognition model according to the embodiments of the present disclosure, the determining a target loss function according to the first predicted probability, the second predicted probability, the third predicted probability, and the fourth predicted probability may include:

calculating the first loss function according to the first predicted probability and labeled information corresponding to the first image set;

calculating the second loss function according to the second predicted probability and the third predicted probability;

calculating the third loss function according to the fourth predicted probability and labeled information corresponding to the third image set;

obtaining an entropy loss function and a regularization loss function; and obtaining the target loss function through calculation according to the first loss function, the second loss function, the third loss function, the entropy loss function, and the regularization loss function.

In some embodiments, specific content of the target loss function is described. The apparatus for training an image recognition model calculates the first loss function $L_{CE}$ according to the first predicted probability and labeled information corresponding to the first image set. The apparatus for training an image recognition model calculates the second loss function $L_{Con}$ according to at least one second predicted probability and at least one third predicted probability. The apparatus for training an image recognition model calculates the third loss function $L_{MTL}$ according to the third predicted probability and labeled information corresponding to the third image set. In addition, the target loss function further includes an entropy loss function $L_{Ent}$ and a regularization loss function $L_{Reg}$.

The entropy loss function $L_{Ent}$ and the regularization loss function $L_{Reg}$ are described below.

Minimizing the entropy loss function allows the model more certainly to predict a specific class for a particular task, rather than considering that several classes are all possible, entropy representing an expectation of an amount of information for each class.

A calculation manner of the entropy loss function is as follows:

$$L_{Ent}(p) = -\sum_{k=0}^{C-1} p[k]\log(p[k]),$$

where $L_{Ent}$ represents the entropy loss function, C represents a total quantity of types, k represents a $k^{th}$ type, and p represents a predicted probability.

To avoid overfitting of the model and improve the generalization ability of the model, the regularization loss function may be added to the target loss function. It may be understood that the regularization loss function includes, but is not limited to, an L1 regularization loss function and an L2 regularization loss function. The regularization loss function may be considered as a penalty term of the target loss function.

Based on the above description, the target loss function in the present disclosure may be represented as:

$$L_{total} = w_0 \cdot L_{CE} + w_1 \cdot L_{MTL} + w_2 \cdot L_{Con} + w_3 \cdot L_{Ent} + w_4 \cdot L_{Reg},$$

where $L_{total}$ represents the target loss function, $L_{CE}$ represents the first loss function, $L_{Con}$ represents the second loss function, $L_{MTL}$ represents the third loss function, $L_{Ent}$ represents the entropy loss function, $L_{Reg}$ represents the regularization loss function, $w_0$ represents a first weight, $w_1$ represents a second weight, $w_2$ represents a third weight, $w_3$ represents a fourth weight, and $w_4$ represents a fifth weight. Each item may have different weights (that is, a weight may be a constant value or dynamically changed) when being superimposed. Generally, the weights need to be adjusted according to different tasks and different data sets.

Secondly, in this embodiment of the present disclosure, the specific content of the target loss function is provided, that is, the target loss function includes the first loss function, the second loss function, the third loss function, the entropy loss function, and the regularization loss function. In the foregoing manner, the model is trained in different dimensions by using loss functions of different types, thereby improving the model training accuracy.

Optionally, based on the embodiment corresponding to FIG. 3, in a sixth optional embodiment of the method for training an image recognition model according to the embodiments of the present disclosure, the calculating the first loss function according to the first predicted probability and labeled information corresponding to the first image set may include:

calculating the first loss function in the following manner:

$$L_{CE}(p_0, y_0) = -\log(p_0[y_0]),$$

where $L_{CE}$ represents the first loss function, $p_0$ represents the first predicted probability, and $y_0$ represents the labeled information corresponding to the first image set.

In some embodiments, a calculation manner of the first loss function is described. The apparatus for training an image recognition model may calculate a first loss function according to a first predicted probability obtained through prediction and real labeled information corresponding to the first image set, the first loss function being a cross entropy loss function. It may be understood that in an actual application, the first loss function may be alternatively a loss function of another type, and the cross entropy loss function is used as an example herein for description.

calculating the first loss function in the following manner:

$$L_{CE}(p_0, y_0) = -\log(p_0[y_0]),$$

where $p_0$ represents the first predicted probability. It is assumed that the first predicted probability is a probability generated for a task of labeling a degree of tumor degradation, a label 1 represents a benign tumor, a label 2 represents a malignant tumor, and a label 3 represents no tumor. It is assumed that a first predicted probability of a first image is (0.1, 0.2, 0.7), that is, a prediction label of the first image is obtained as the label 3, which is a label of no tumor. Labeling processing has been performed on the first image, so that labeled information Y°, that is, a real label, may be obtained. It is assumed that the real label is the label 3, a probability corresponding to the label 3 is (0, 0.1). A distance between distributions of two probabilities is described by using the cross entropy loss function, and a smaller cross entropy indicates that the two probabilities are closer. An objective of the model training is to expect that distributions of a predicted probability and a real probability are closer.

Secondly, in this embodiment of the present disclosure, the calculation manner of the first loss function is provided. In the foregoing manner, a specific implementation basis is provided for generation of the first loss function, thereby improving the feasibility and operability of the model training.

Optionally, based on the embodiment corresponding to FIG. 3, in a seventh optional embodiment of the method for training an image recognition model according to the embodiments of the present disclosure, the calculating the second loss function according to the second predicted probability and the third predicted probability may include:

calculating the second loss function in the following manner:

$$L_{Con}(p_s, p_r) = \frac{1}{C}\sum_{k=0}^{C-1}(p_s[k] - p_r[k])^2, \text{ or}$$

calculating the second loss function in the following manner:

$$L_{Con}(p_s, p_r) = \sum_{k=0}^{C-1}p_s[k]\ln\left(\frac{p_s[k]}{p_r[k]}\right),$$

where $L_{Con}$ represents the second loss function, C represents a total quantity of types, k represents a $k^{th}$ type, represents the second predicted probability, and $p_r$ represents the third predicted probability.

In some embodiments, a calculation manner of the second loss function is described. The apparatus for training an image recognition model may calculate a second loss function according to a second predicted probability and a third predicted probability that are obtained through prediction. The second loss function may be a mean-square error (MSE) loss function or may be a kullback-leibler (KL) divergence loss function. It may be understood that in an actual application, the second loss function may be alternatively a loss function of another type, and the MSE loss function and the KL divergence loss function are used as examples herein for description.

When the second loss function is the MSE loss function, the second loss function is calculated in the following manner:

$$L_{Con}(p_s, p_r) = \frac{1}{C}\sum_{k=0}^{C-1}(p_s[k] - p_r[k])^2,$$

When the second loss function is the KL divergence loss function, the second loss function is calculated in the following manner:

$$L_{Con}(p_s, p_r) = \sum_{k=0}^{C-1}p_s[k]\ln\left(\frac{p_s[k]}{p_r[k]}\right),$$

A calculation manner of the second predicted probability $p_s$ is as follows:

$$p_s[i] = \frac{e^{z_s[i]}}{\sum_{k=0}^{C-1}e^{z_s[k]}},$$

where $p_s$ represents the second predicted probability, $p_s[i]$ represents an $i^{th}$ unit in the second predicted probability, C represent a total quantity of types, k represents a $k^{th}$ type, and a value of i is an integer greater than or equal to 0 and less than or equal to C−1.

A calculation manner of the third predicted probability $p_r$ is as follows:

$$p_r[i] = \frac{e^{z_r[i]}}{\sum_{k=0}^{C-1}e^{z_r[k]}},$$

where $p_r$ represents the third predicted probability, $p_r[i]$ represents an $i^{th}$ unit in the third predicted probability, C represents a total quantity of types, k represents a $k^{th}$ type, and a value of i is an integer greater than or equal to 0 and less than or equal to C−1.

It may be understood that the second predicted probability and the third predicted probability may be outputted in the same training. Therefore, the second predicted probability may be alternatively represented as $p_0$, and $p_r$ represents the third predicted probability. Similarly, the third predicted probability $p_r$ is obtained after normalization processing is performed on a predicted value $z_r$. The second predicted probability and the third predicted probability are alternatively outputted in different times of training. The second loss function may be specifically a consistency loss function, and a smaller second loss function indicates that results of two predictions are closer, that is, an effect of model training is better, and minimizing the second loss function allows two predicted values to be consistent.

Secondly, in this embodiment of the present disclosure, the calculation manner of the second loss function is provided. In the foregoing manner, a specific implementation basis is provided for generation of the second loss function, thereby improving the feasibility and operability of the model training. In addition, an appropriate second loss function may be further selected for calculation according to a requirement, thereby improving the flexibility of the solution.

Optionally, based on the embodiment corresponding to FIG. 3, in an eighth optional embodiment of the method for training an image recognition model according to the embodiments of the present disclosure, the calculating the third loss function according to the fourth predicted probability and labeled information corresponding to the third image set includes:

calculating the third loss function in the following manner:

$$L_{MTL}(p_1, y_1) = -\log(p_1[y_1]),$$

where $L_{MTL}$ represents the third loss function, $p_1$ represents the fourth predicted probability, and $y_1$ represents the labeled information corresponding to the third image set.

In some embodiments, a calculation manner of the third loss function is described. The apparatus for training an image recognition model may calculate a third loss function according to a third predicted probability obtained through prediction and real labeled information corresponding to the third image set, the third loss function being a cross entropy loss function. It may be understood that in an actual application, the third loss function may be alternatively a loss function of another type, and the cross entropy loss function is used as an example herein for description.

calculating the third loss function in the following manner:

$$L_{MTL}(p_1, y_1) = -\log(p_1[y_1]),$$

where $p_1$ represents the fourth predicted probability. It is assumed that the fourth predicted probability is a probability generated for a task of labeling a qualified condition of a picture, a label 1 represents that a picture is qualified, and a label 2 represents that a picture is not qualified. It is assumed that a fourth predicted probability of a third image is (0.2, 0.8), that is, a prediction label of the third image is obtained as the label 2, which is a label in which the picture is not qualified. Labeling processing has been performed on the third image, so that labeled information $y_1$, that is, a real label, may be obtained. It is assumed that the real label is the label 1, a probability corresponding to the label 1 is (1, 0). A distance between distributions of two probabilities is described by using the cross entropy loss function, and a smaller cross entropy indicates that the two probabilities are closer. An objective of the model training is to expect that distributions of a predicted probability and a real probability are closer.

Secondly, in this embodiment of the present disclosure, the calculation manner of the third loss function is provided. In the foregoing manner, a specific implementation basis is provided for generation of the third loss function, thereby improving the feasibility and operability of the model training.

Figure 6:
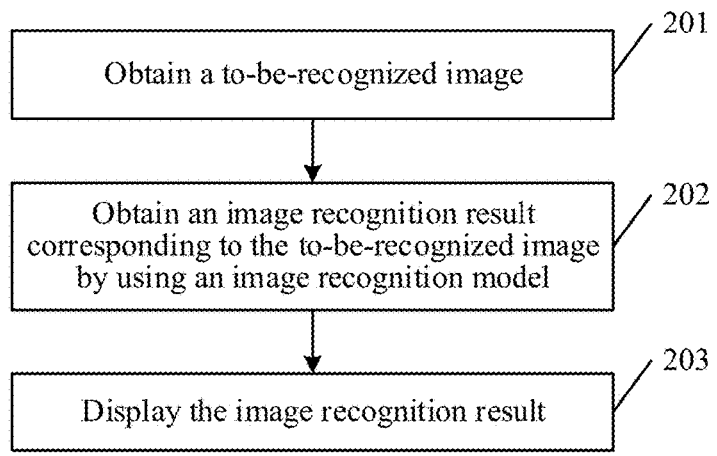
FIG. 6 is a schematic diagram of an embodiment of an image recognition method according to an embodiment of the present disclosure.

With reference to the foregoing description, the present disclosure further provides an image recognition method. Referring to FIG. 6, an embodiment of an image recognition method in this embodiment of the present disclosure includes the following steps.

201. Obtain a to-be-recognized image.

In some embodiments, an image recognition apparatus obtains a to-be-recognized image. The to-be-recognized image may be an endoscope image or may be a medical image of another type. This is not limited herein. The image recognition apparatus may be deployed in the server or may be deployed in the terminal device. Herein, an example in which the image recognition apparatus is deployed in the terminal device is used for description, but is not to be understood as a limitation to the present disclosure.

202. Obtain an image recognition result corresponding to the to-be-recognized image by using an image recognition model, the image recognition model being the image recognition model according to the foregoing embodiments.

In some embodiments, the image recognition apparatus inputs the to-be-recognized image into the image recognition model described in the foregoing embodiments, and the image recognition model outputs a corresponding image recognition result.

203. Display the image recognition result.

Figure 7:
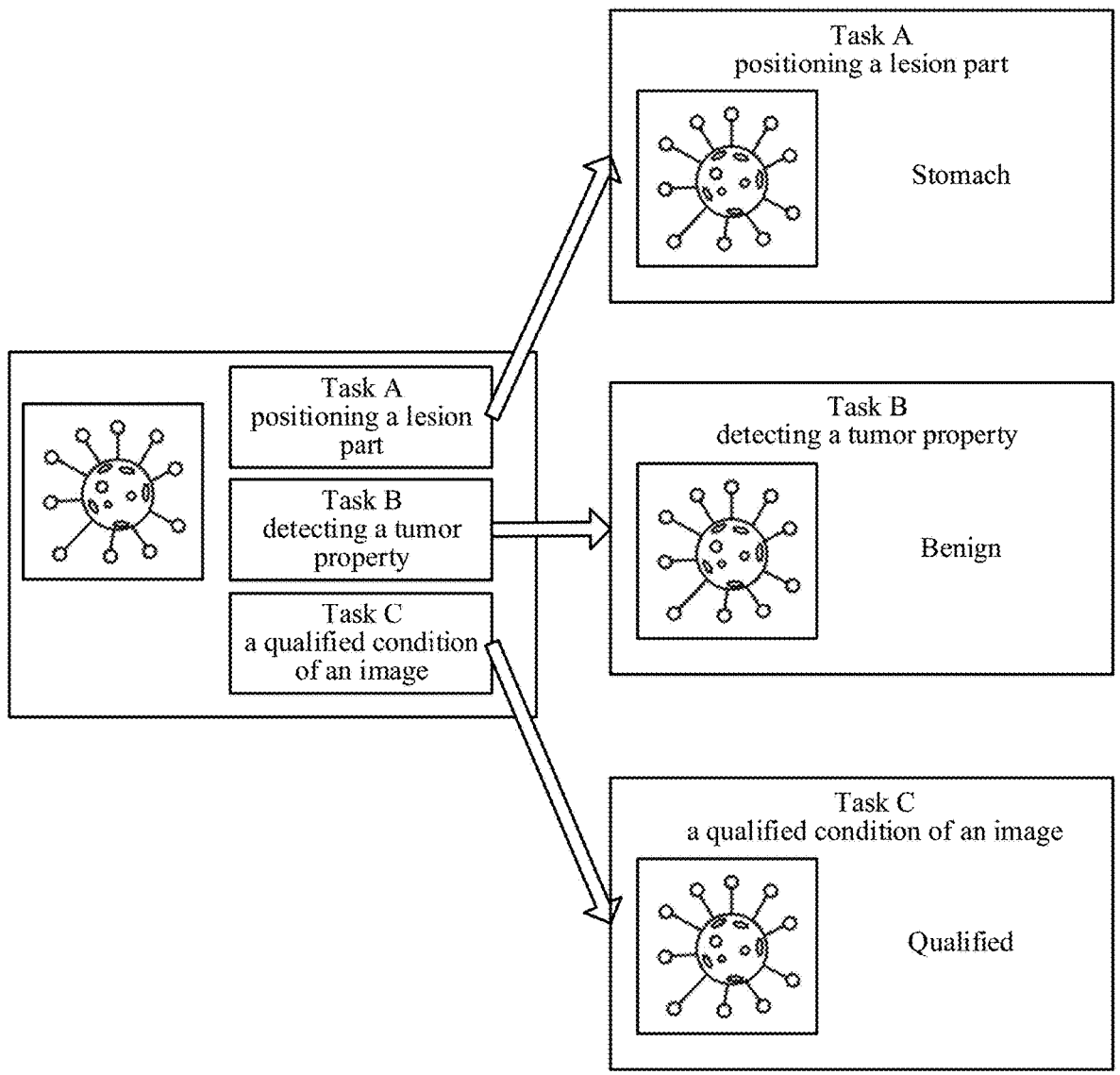
FIG. 7 is a schematic diagram of an interface of displaying an image recognition result according to an embodiment of the present disclosure.

In some embodiments, the image recognition apparatus may display the image recognition result. For ease of understanding, FIG. 7 is a schematic diagram of an interface of displaying an image recognition result according to an embodiment of the present disclosure. As shown in the figure, an inputted medical image is used as an example, and a doctor may select a corresponding task according to a requirement. It is assumed that a task A, that is, a task of positioning a lesion part is selected, a corresponding result is outputted based on the task A selected by the doctor, for example, a positioned lesion part is "stomach". It is assumed that a task B, that is, a task of detecting a property of a tumor, is selected, a corresponding result is outputted based on the task B selected by the doctor, for example, a property of a tumor is detected as "benign". It is assumed that a task C, that is, a task of a qualified condition of an image, is selected, a corresponding result is outputted based on the task C selected by the doctor, for example, a qualified condition of an image is "qualified".

In this embodiment of the present disclosure, the image recognition method is provided, that is, a to-be-recognized image is obtained first, then the to-be-recognized image is inputted into a trained image recognition model, the image recognition model outputs an image recognition result, and finally the image recognition result is displayed. In the foregoing manner, when automatic diagnosis is performed by using the image recognition model provided in the present disclosure, a recognition result under a corresponding task may be displayed according to a requirement, to assist a doctor in diagnosis, thereby more effectively helping the doctor reduce misdiagnosis and missed diagnosis, especially for a doctor lack of relevant clinical experience.

Figure 8:
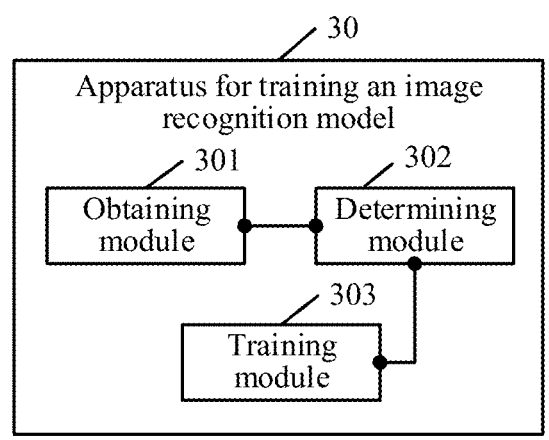
FIG. 8 is a schematic diagram of an embodiment of an apparatus for training an image recognition model according to an embodiment of the present disclosure.

The apparatus for training an image recognition model in the present disclosure is described in detail below. FIG. 8 is a schematic diagram of an embodiment of an apparatus for training an image recognition model according to an embodiment of the present disclosure. An apparatus 30 for training an image recognition model includes:

an obtaining module 301, configured to obtain training image sets, the training image sets including at least a first image set, a second image set, and a third image set, the first image set including at least one first image, the second image set including at least one second image and at least one perturbed image, the third image set including at least one third image, the first image being a labeled image corresponding to a first task, the second image being an unlabeled image corresponding to the first task, the third image being a labeled image corresponding to a second task, the first task and the second task being different tasks;

the obtaining module 301, further configured to obtain a first predicted probability, a second predicted probability, a third predicted probability, and a fourth predicted probability based on the training image sets by using an initial image recognition model, the first predicted probability being a predicted result outputted based on the first image set, the second predicted probability and the third predicted probability being predicted results outputted based on the second image set, and the fourth predicted probability being a predicted result outputted based on the third image set;

a determining module 302, configured to determine a target loss function according to the first predicted probability, the second predicted probability, the third predicted probability, and the fourth predicted probability that are obtained by the obtaining module 301, the target loss function including at least a first loss function, a second loss function, and a third loss function, the first loss function being determined according to the first predicted probability, the second loss function being determined according to the second predicted probability and the third predicted probability, and the third loss function being determined according to the fourth predicted probability; and a training module 303, configured to train the initial image recognition model according to the target loss function determined by the determining module 302, to obtain an image recognition model.

The embodiments of the present disclosure provide an apparatus for training an image recognition model. Training image sets are obtained first, then a first predicted probability, a second predicted probability, a third predicted probability, and a fourth predicted probability are obtained based on the training image sets by using an initial image recognition model, subsequently, a target loss function is determined according to the first predicted probability, the second predicted probability, the third predicted probability, and the fourth predicted probability, and finally the initial image recognition model is trained based on the target loss function, to obtain an image recognition model. In the foregoing manner, a model is trained by using a labeled medical image for different tasks and an unlabeled medical image together. The labeled image and the unlabeled image are effectively used, so that a requirement for image labeling is reduced and a data volume for training is increased, thereby improving a model prediction effect while saving labeling resources.

Optionally, based on the embodiment corresponding to FIG. 8, in another embodiment of the apparatus 30 for training an image recognition model in this embodiment of the present disclosure, the obtaining module 301 is further configured to:

obtain the first predicted probability based on the first image set by using the initial image recognition model;

obtain the second predicted probability and the third predicted probability based on the second image set by using the initial image recognition model; and obtain the fourth predicted probability based on the third image set by using the initial image recognition model.

Secondly, in this embodiment of the present disclosure, a method for obtaining the first predicted probability, the second predicted probability, the third predicted probability, and the fourth predicted probability is provided. The second predicted probability and the third predicted probability are obtained based on the second image set by using the semi-supervised learning, and the fourth predicted probability is obtained based on the third image set by using the MTL. In the foregoing manner, training is effectively performed by using unlabeled data, to improve a model effect, and a requirement for labeled data is reduced while a better effect is obtained, thereby reducing product development costs and accelerating a product development cycle. In addition, a plurality of related tasks can be further trained at the same time by using one image recognition model, some parameters of the image recognition model are shared by various tasks, and some other parameters are unique to each task. Shared parameters use all data sets of all tasks, so that a data volume for training is increased, and meanwhile unique noise of each training set is canceled, thereby improving a generalization ability of the model, and reducing overfitting of the model. An independent output layer may select a most relevant feature for a task from a shared part, and learn a unique classification boundary of each task, so that the model has sufficient flexibility, and can obtain relatively high accuracy for an image recognition task.

Optionally, based on the embodiment corresponding to FIG. 8, in another embodiment of the apparatus 30 for training an image recognition model in this embodiment of the present disclosure, the obtaining module 301 is further configured to obtain a first predicted value based on the at least one first image by using an FC layer included in the initial image recognition model;

and perform normalization processing on the first predicted value, to obtain the first predicted probability.

Secondly, in this embodiment of the present disclosure, a method for generating the first predicted probability is provided, that is, first, a first predicted value of the first image is obtained by using an FC layer included in the initial image recognition model, and then normalization processing is performed on the first predicted value of the first image, to obtain the first predicted probability of the first image. In the foregoing manner, after normalization processing is performed on a predicted value, a prediction class of a sample can be reflected more intuitively, thereby improving the accuracy of training sample classification and improving the model training efficiency and accuracy.

Optionally, based on the embodiment corresponding to FIG. 8, in another embodiment of the apparatus 30 for training an image recognition model in this embodiment of the present disclosure, the obtaining module 301 is further configured to:

generate a first perturbed image set according to the at least one second image, the first perturbed image set including at least one first perturbed image, the first perturbed image having a correspondence with the second image, and the first perturbed image being the perturbed image;

generate a second perturbed image set according to the at least one second image, the second perturbed image set including at least one second perturbed image, the second perturbed image having a correspondence with the second image, and the second perturbed image being the perturbed image;

obtain the second predicted probability based on the at least one second image and the first perturbed image set by using the initial image recognition model; and obtain the third predicted probability based on the at least one second image and the second perturbed image set by using the initial image recognition model.

Secondly, in this embodiment of the present disclosure, the data processing manner based on semi-supervised learning is provided, that is, two times of random scrambling are performed on a second image, to obtain a first perturbed image and a second perturbed image, and then the second image and each of the first perturbed image and the second perturbed image form two training samples to be inputted into a model, to obtain two predicted probabilities. In the foregoing manner, random scrambling can be effectively performed on an unlabeled image, to obtain images with different perturbed degrees as samples for model training, and manual intervention is not required during random scrambling, thereby improving the model training efficiency. In addition, randomized processing can improve a generalization ability of a model, thereby improving a model training effect. The semi-supervised learning avoids waste of data and resources, and resolves problems that a generalization ability of a model of full supervised learning is not strong and a model of unsupervised learning is inaccurate.

Optionally, based on the embodiment corresponding to FIG. 8, in another embodiment of the apparatus 30 for training an image recognition model in this embodiment of the present disclosure, the obtaining module 301 is further configured to:

obtain a fourth predicted value based on the at least one third image by using a fully connected layer included in the initial image recognition model; and perform normalization processing on the fourth predicted value, to obtain the fourth predicted probability.

Secondly, in this embodiment of the present disclosure, a method for generating the fourth predicted probability is provided, that is, first, a second predicted value of the third image is obtained by using the FC layer included in the initial image recognition model, and then normalization processing is performed on the second predicted value of the third image, to obtain the fourth predicted probability of the third image. In the foregoing manner, after normalization processing is performed on a predicted value, a prediction class of a sample can be reflected more intuitively, thereby improving the accuracy of training sample classification and improving the model training efficiency and accuracy.

Optionally, based on the embodiment corresponding to FIG. 8, in another embodiment of the apparatus 30 for training an image recognition model in this embodiment of the present disclosure, the determining module 302 is further configured to:

calculate the first loss function according to the first predicted probability and labeled information corresponding to the first image set;

calculate the second loss function according to the second predicted probability and the third predicted probability;

calculate the third loss function according to the fourth predicted probability and labeled information corresponding to the third image set;

obtain an entropy loss function and a regularization loss function; and obtain the target loss function through calculation according to the first loss function, the second loss function, the third loss function, the entropy loss function, and the regularization loss function.

Secondly, in this embodiment of the present disclosure, the specific content of the target loss function is provided, that is, the target loss function includes the first loss function, the second loss function, the third loss function, the entropy loss function, and the regularization loss function. In the foregoing manner, the model is trained in different dimensions by using loss functions of different types, thereby improving the model training accuracy.

Optionally, based on the embodiment corresponding to FIG. 8, in another embodiment of the apparatus 30 for training an image recognition model in this embodiment of the present disclosure, the determining module 302 is further configured to calculate the first loss function in the following manner:

$$L_{CE}(p_0, y_0) = -\log(p_0[y_0]),$$

where $L_{CE}$ represents the first loss function, $p_0$ represents the first predicted probability, and $y_0$ represents the labeled information corresponding to the first image set.

Secondly, in this embodiment of the present disclosure, the calculation manner of the first loss function is provided. In the foregoing manner, a specific implementation basis is provided for generation of the first loss function, thereby improving the feasibility and operability of the model training.

Optionally, based on the embodiment corresponding to FIG. 8, in another embodiment of the apparatus 30 for training an image recognition model in this embodiment of the present disclosure, the determining module 302 is further configured to:

calculate the second loss function in the following manner:

$$L_{Con}(p_s, p_r) = \frac{1}{C}\sum_{k=0}^{C-1}(p_s[k] - p_r[k])^2,$$

calculate the second loss function in the following manner:

$$L_{Con}(p_s, p_r) = \sum_{k=0}^{C-1}p_s[k]\ln\left(\frac{p_s[k]}{p_r[k]}\right),$$

where $L_{Con}$ represents the second loss function, C represents a total quantity of types, k represents a $k^{th}$ type, $p_s$ represents the second predicted probability, and $p_r$ represents the third predicted probability.

Secondly, in this embodiment of the present disclosure, the calculation manner of the second loss function is provided. In the foregoing manner, a specific implementation basis is provided for generation of the second loss function, thereby improving the feasibility and operability of the model training. In addition, an appropriate second loss function may be further selected for calculation according to a requirement, thereby improving the flexibility of the solution.

Optionally, based on the embodiment corresponding to FIG. 8, in another embodiment of the apparatus 30 for training an image recognition model in this embodiment of the present disclosure, the determining module 302 is further configured to:

calculate the third loss function in the following manner:

$$L_{MTL}(p_1, y_1) = -\log(p_1[y_1]),$$

where $L_{MTL}$ represents the third loss function, $p_1$ represents the fourth predicted probability, and $y_1$ represents the labeled information corresponding to the third image set.

Secondly, in this embodiment of the present disclosure, the calculation manner of the third loss function is provided. In the foregoing manner, a specific implementation basis is provided for generation of the third loss function, thereby improving the feasibility and operability of the model training.

Figure 9:
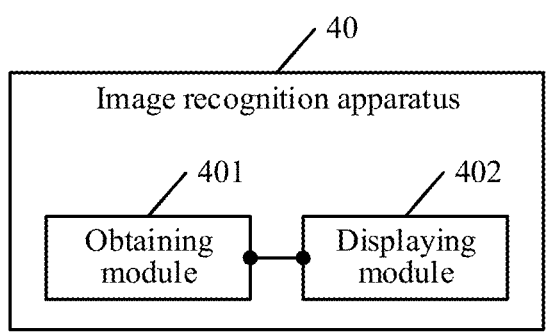
FIG. 9 is a schematic diagram of an embodiment of an image recognition apparatus according to an embodiment of the present disclosure.

The image recognition apparatus in the present disclosure is described below in detail. FIG. 9 is a schematic diagram of an embodiment of an image recognition apparatus according to an embodiment of the present disclosure, and an image recognition apparatus 40 includes:

an obtaining module 401, configured to obtain a to-be-recognized image;

the obtaining module 401, further configured to obtain an image recognition result corresponding to the to-be-recognized image by using an image recognition model, the image recognition model being the image recognition model provided by the embodiments corresponding to FIG. 3; and a displaying module 402, configured to display the image recognition result obtained by the obtaining module 401.

In this embodiment of the present disclosure, an image recognition apparatus is provided, that is, a to-be-recognized image is obtained first, subsequently, the to-be-recognized image is inputted into a trained image recognition model, the image recognition model outputs an image recognition result, and finally the image recognition result is displayed. In the foregoing manner, when automatic diagnosis is performed by using the image recognition model provided in the present disclosure, a recognition result under a corresponding task may be displayed according to a requirement, to assist a doctor in diagnosis, thereby more effectively helping the doctor reduce misdiagnosis and missed diagnosis, especially for a doctor lack of relevant clinical experience.

The term unit (and other similar terms such as subunit, module, submodule, etc.) in this disclosure may refer to a software unit, a hardware unit, or a combination thereof. A software unit (e.g., computer program) may be developed using a computer programming language. A hardware unit may be implemented using processing circuitry and/or memory. Each unit can be implemented using one or more processors (or processors and memory). Likewise, a processor (or processors and memory) can be used to implement one or more units. Moreover, each unit can be part of an overall unit that includes the functionalities of the unit.

The apparatus for training an image recognition model and the image recognition apparatus provided in the present disclosure may be deployed in an electronic device, and the electronic device may be a server or may be a terminal device.

Figure 10:
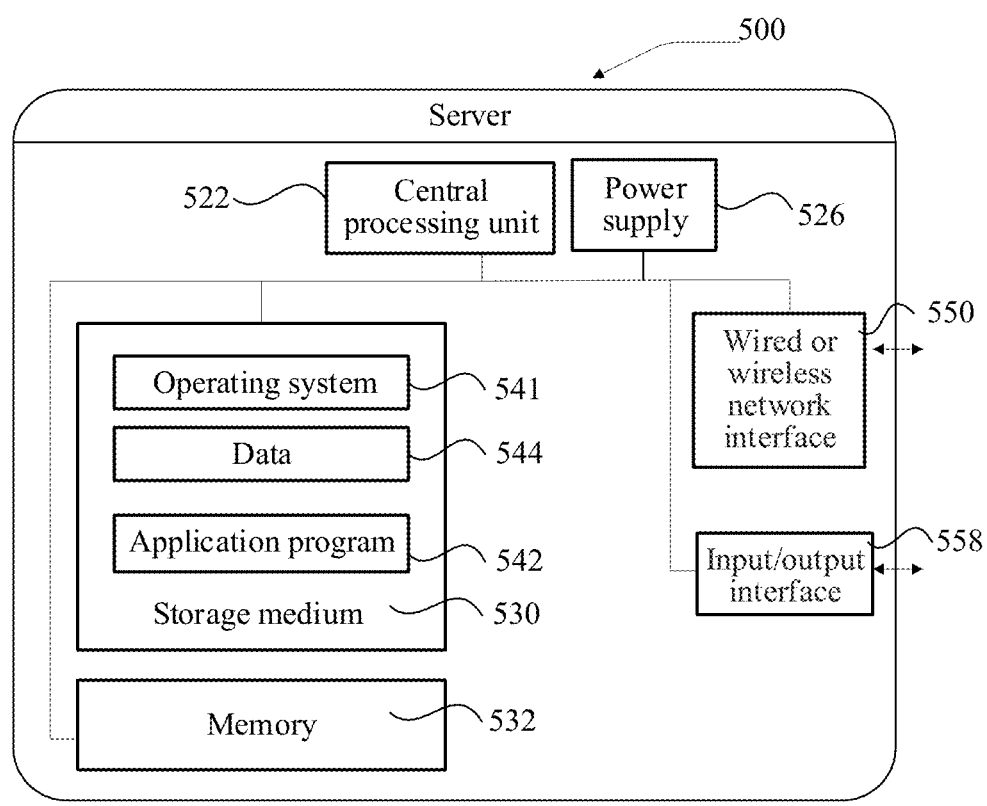
FIG. 10 is a schematic structural diagram of a server according to an embodiment of the present disclosure.

FIG. 10 is a schematic structural diagram of a server according to an embodiment of the present disclosure. The server 500 may vary greatly due to different configurations or performance, and may include one or more central processing units (CPU) 522 (for example, one or more processors) and a memory 532, and one or more storage media 530 (for example, one or more mass storage devices) that store application programs 542 or data 544. The memory 532 and the storage media 530 may be temporary storage or persistent storage. A program stored in the storage media 530 may include one or more modules (which are not marked in the figure), and each module may include a series of instruction operations on the server. Still further, the CPU 522 may be configured to communicate with the storage medium 530 to perform the series of instruction operations in the storage medium 530 on the server 500.

The server 500 may further include one or more power supplies 526, one or more wired or wireless network interfaces 550, one or more input/output interfaces 558, and/or one or more operating systems 541 such as Windows Server™, Mac OS X™, Unix™, Linux™, or FreeBSD™.

The steps performed by the server in the foregoing embodiment may be based on the structure of the server shown in FIG. 10.

In this embodiment of the present disclosure, the CPU 522 included in the server further has the following functions:

obtaining training image sets, the training image sets including at least a first image set, a second image set, and a third image set, the first image set including at least one first image, the second image set including at least one second image and at least one perturbed image, the third image set including at least one third image, the first image being a labeled image corresponding to a first task, the second image being an unlabeled image corresponding to the first task, the third image being a labeled image corresponding to a second task, the first task and the second task being different tasks;

obtaining a first predicted probability, a second predicted probability, a third predicted probability, and a fourth predicted probability based on the training image sets by using an initial image recognition model, the first predicted probability being a predicted result outputted based on the first image set, the second predicted probability and the third predicted probability being predicted results outputted based on the second image set, and the fourth predicted probability being a predicted result outputted based on the third image set;

determining a target loss function according to the first predicted probability, the second predicted probability, the third predicted probability, and the fourth predicted probability, the target loss function including at least a first loss function, a second loss function, and a third loss function, the first loss function being determined according to the first predicted probability, the second loss function being determined according to the second predicted probability and the third predicted probability, and the third loss function being determined according to the fourth predicted probability; and training the initial image recognition model based on the target loss function, to obtain an image recognition model.

In this embodiment of the present disclosure, the CPU 522 included in the server further has the following functions:

obtaining a to-be-recognized image;

obtaining an image recognition result corresponding to the to-be-recognized image by using an image recognition model, the image recognition model being the image recognition model according to the embodiments corresponding to FIG. 3; and displaying the image recognition result.

Figure 11:
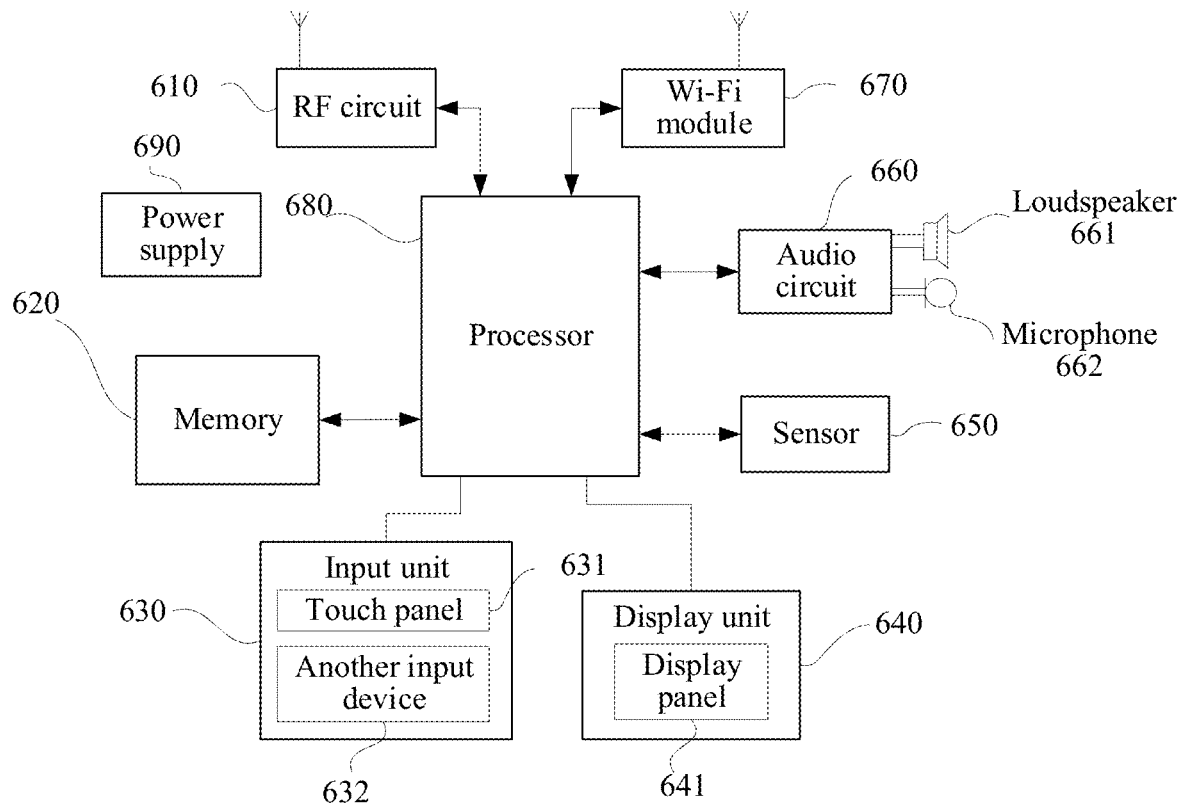
FIG. 11 is a schematic structural diagram of a terminal device according to an embodiment of the present disclosure.

This embodiment of the present disclosure further provides another apparatus for training an image recognition model and another image recognition apparatus shown in FIG. 11. For ease of description, only parts related to this embodiment of the present disclosure are shown. For specific technical details that are not disclosed, reference is made to the method part of the embodiments of the present disclosure. The terminal device may be any terminal device including a mobile phone, a tablet computer, a personal digital assistant (PDA), a point of sales (POS), an on-board computer, or the like, and the terminal device being a mobile phone is used as an example.

FIG. 11 is a block diagram of a structure of a part of a mobile phone related to a terminal device according to an embodiment of the present disclosure. Referring to FIG. 11, the mobile phone includes components such as: a radio frequency (RF) circuit 610, a memory 620, an input unit 630, a display unit 640, a sensor 650, an audio circuit 660, a wireless fidelity (WiFi) module 670, a processor 680, and a power supply 690. The input unit 630 may include a touch panel 631 and another input device 632, the display unit 640 may include a display panel 641, and the audio circuit 660 is connected to a loudspeaker 661 and a microphone 662. A person skilled in the art can understand that the structure of the mobile phone shown in FIG. 11 does not constitute a limitation to the mobile phone, and the mobile phone may include more components or fewer components than those shown in the figure, or some components may be combined, or a different component deployment may be used.

The memory 620 may be configured to store a software program and module. The processor 680 runs the software program and module stored in the memory 620, to implement various functional applications and data processing of the mobile phone. The memory 620 may mainly include a program storage area and a data storage area. The program storage area may store an operating system, an application program required by at least one function (such as a sound playback function and an image display function), and the like. The data storage area may store data (for example, audio data and an address book) created according to the use of the mobile phone, and the like.

The processor 680 is a control center of the mobile phone, and is connected to various parts of the entire mobile phone by using various interfaces and lines. By running or executing a software program and/or module stored in the memory 620, and invoking data stored in the memory 620, the processor executes various functions of the mobile phone and performs data processing, thereby monitoring the entire mobile phone.

In this embodiment of the present disclosure, the processor 680 included in the terminal device further has the following functions:

obtaining training image sets, the training image sets including at least a first image set, a second image set, and a third image set, the first image set including at least one first image, the second image set including at least one second image and at least one perturbed image, the third image set including at least one third image, the first image being a labeled image corresponding to a first task, the second image being an unlabeled image corresponding to the first task, the third image being a labeled image corresponding to a second task, the first task and the second task being different tasks;

obtaining a first predicted probability, a second predicted probability, a third predicted probability, and a fourth predicted probability based on the training image sets by using an initial image recognition model, the first predicted probability being a predicted result outputted based on the first image set, the second predicted probability and the third predicted probability being predicted results outputted based on the second image set, and the fourth predicted probability being a predicted result outputted based on the third image set;

determining a target loss function according to the first predicted probability, the second predicted probability, the third predicted probability, and the fourth predicted probability, the target loss function including at least a first loss function, a second loss function, and a third loss function, the first loss function being determined according to the first predicted probability, the second loss function being determined according to the second predicted probability and the third predicted probability, and the third loss function being determined according to the fourth predicted probability; and training the initial image recognition model based on the target loss function, to obtain an image recognition model.

In this embodiment of the present disclosure, the processor 680 included in the terminal device further has the following functions:

obtaining a to-be-recognized image;

obtaining an image recognition result corresponding to the to-be-recognized image by using an image recognition model, the image recognition model being the image recognition model according to the embodiments corresponding to FIG. 3; and displaying the image recognition result.

Figure 12:
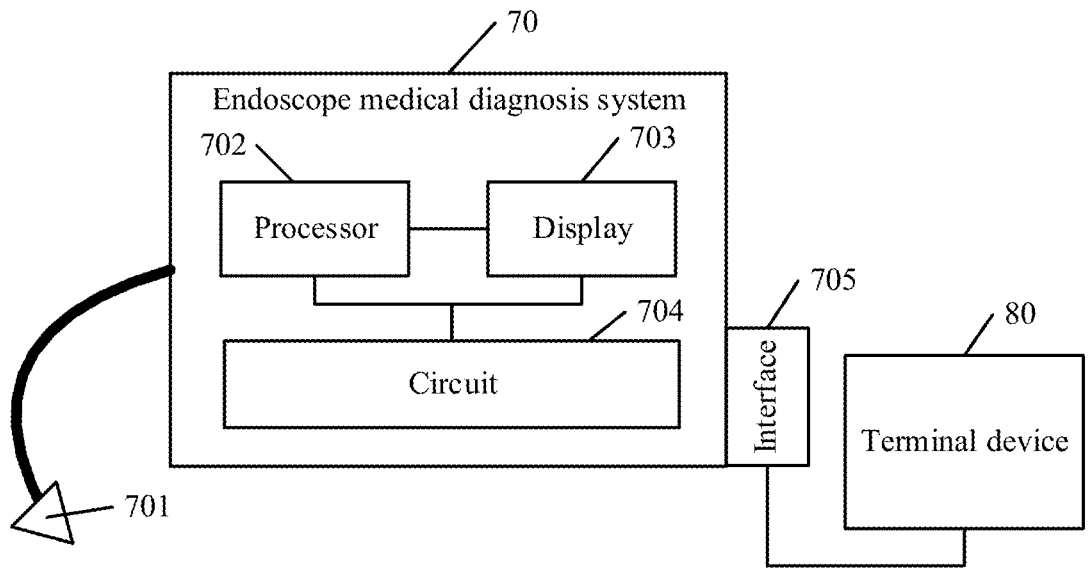
FIG. 12 is a schematic structural diagram of an endoscope medical diagnosis system according to an embodiment of the present disclosure.

FIG. 12 is a structural diagram of an endoscope medical diagnosis system 70 according to an implementation of the present disclosure. The endoscope medical diagnosis system 70 in this implementation is a system for supporting an endoscope service. The endoscope medical diagnosis system 70 has a probe 701, a processor 702, a display 703, a circuit 704, and an interface 705. The endoscope medical diagnosis system 70 and a terminal device 80 can work cooperatively. The probe 701 may be specifically an endoscope probe, and may be inserted into the esophagus, gastrointestinal, bronchial, or the like for real-time scanning imaging. A doctor can clearly identify a tumor growth level and a depth of invasion by using the endoscope probe. In addition, the endoscope probe may be further applied to organ imaging in the vicinity of the intestinal tract, and plays a role in lesion diagnosis of pancreas, bile duct, and gall bladder.

The processor 702 is configured to recognize an endoscope image captured by the probe 701 and generate a recognition result. The display 703 displays a lesion recognition result according to an image signal inputted by the processor 702, the lesion recognition result being specifically an image result, and may display an image in real time captured by the probe 701. The circuit 704 is configured to be connected to modules in the endoscope medical diagnosis system 70 and provide an electrical signal, to enable normal operation inside the endoscope medical diagnosis system 70 and enable the endoscope medical diagnosis system to establish a communication connection with the terminal device 80.

The endoscope medical diagnosis system 70 may directly recognize and process an acquired endoscope image, or send an acquired endoscope image to the terminal device 80 by using the interface 705, and the terminal device 80 recognizes and processes the endoscope image. The terminal device 80 can make an electronic medical record and a prescription or directly print an electronic medical record and a prescription, or the like based on a lesion recognition result sent by the endoscope medical diagnosis system 70.

In this embodiment of the present disclosure, the processor 702 included in the endoscope medical diagnosis system further has the following functions:

obtaining training image sets, the training image sets including at least a first image set, a second image set, and a third image set, the first image set including at least one first image, the second image set including at least one second image and at least one perturbed image, the third image set including at least one third image, the first image being a labeled image corresponding to a first task, the second image being an unlabeled image corresponding to the first task, the third image being a labeled image corresponding to a second task, the first task and the second task being different tasks;

obtaining a first predicted probability, a second predicted probability, a third predicted probability, and a fourth predicted probability based on the training image sets by using an initial image recognition model, the first predicted probability being a predicted result outputted based on the first image set, the second predicted probability and the third predicted probability being predicted results outputted based on the second image set, and the fourth predicted probability being a predicted result outputted based on the third image set;

determining a target loss function according to the first predicted probability, the second predicted probability, the third predicted probability, and the fourth predicted probability, the target loss function including at least a first loss function, a second loss function, and a third loss function, the first loss function being determined according to the first predicted probability, the second loss function being determined according to the second predicted probability and the third predicted probability, and the third loss function being determined according to the fourth predicted probability; and training the initial image recognition model based on the target loss function, to obtain an image recognition model.

Optionally, the processor 702 included in the endoscope medical diagnosis system is further configured to perform the following steps:

obtaining the first predicted probability based on the first image set by using the initial image recognition model;

obtaining the second predicted probability and the third predicted probability based on the second image set by using the initial image recognition model; and obtaining the fourth predicted probability based on the third image set by using the initial image recognition model.

Optionally, the processor 702 included in the endoscope medical diagnosis system is further configured to perform the following steps:

obtaining a first predicted value based on the at least one first image by using an FC layer included in the initial image recognition model; and performing normalization processing on the first predicted value, to obtain the first predicted probability.

Optionally, the processor 702 included in the endoscope medical diagnosis system is further configured to perform the following steps:

generating a first perturbed image set according to the at least one second image, the first perturbed image set including at least one first perturbed image, the first perturbed image having a correspondence with the second image, and the first perturbed image being the perturbed image;

generating a second perturbed image set according to the at least one second image, the second perturbed image set including at least one second perturbed image, the second perturbed image having a correspondence with the second image, and the second perturbed image being perturbed image;

obtaining the second predicted probability based on the at least one second image and the first perturbed image set by using the initial image recognition model; and obtaining the third predicted probability based on the at least one second image and the second perturbed image set by using the initial image recognition model.

Optionally, the processor 702 included in the endoscope medical diagnosis system is further configured to perform the following steps:

obtaining a fourth predicted value based on the at least one third image by using an FC layer included in the initial image recognition model; and performing normalization processing on the fourth predicted value, to obtain the fourth predicted probability.

Optionally, the processor 702 included in the endoscope medical diagnosis system is further configured to perform the following steps:

calculating the first loss function according to the first predicted probability and labeled information corresponding to the first image set;

calculating the second loss function according to the second predicted probability and the third predicted probability;

calculating the third loss function according to the fourth predicted probability and labeled information corresponding to the third image set;

obtaining an entropy loss function and a regularization loss function; and obtaining the target loss function through calculation according to the first loss function, the second loss function, the third loss function, the entropy loss function, and the regularization loss function.

In this embodiment of the present disclosure, the processor 702 included in the endoscope medical diagnosis system further has the following functions:

obtaining a to-be-recognized image;

obtaining an image recognition result corresponding to the to-be-recognized image by using an image recognition model, the image recognition model being the image recognition model according to the embodiments corresponding to FIG. 3; and displaying the image recognition result.

A person skilled in the art can clearly understand that for convenience and conciseness of description, for specific working processes of the foregoing systems, apparatuses and units, reference may be made to the corresponding processes in the foregoing method embodiments, and details are not described herein again.

What is claimed is:

1. A method for training an image recognition model, performed by an electronic device, the method comprising:

obtaining training image sets, the training image sets comprising at least a first image set, a second image set, and a third image set, the first image set comprising at least one first image, the second image set comprising at least one second image and at least one perturbed image, the third image set comprising at least one third image, the first image being a labeled image corresponding to a first task, the second image being an unlabeled image corresponding to the first task, the third image being a labeled image corresponding to a second task, the first task and the second task being different tasks;

obtaining a first predicted probability, a second predicted probability, a third predicted probability, and a fourth predicted probability based on the training image sets by using an initial image recognition model, the first predicted probability being a predicted result outputted based on the first image set, the second predicted probability and the third predicted probability being predicted results outputted based on the second image set, and the fourth predicted probability being a predicted result outputted based on the third image set;

determining a target loss function according to the first predicted probability, the second predicted probability, the third predicted probability, and the fourth predicted probability, the target loss function comprising at least a first loss function determined according to the first predicted probability, a second loss function determined according to the second predicted probability and the third predicted probability, and a third loss function determined according to the fourth predicted probability; and training the initial image recognition model based on the target loss function, to obtain an image recognition model.

2. The method according to claim 1, wherein the obtaining a first predicted probability, a second predicted probability, a third predicted probability, and a fourth predicted probability based on the training image sets by using an initial image recognition model comprises:
obtaining the first predicted probability based on the first image set by using the initial image recognition model;
obtaining the second predicted probability and the third predicted probability based on the second image set by using the initial image recognition model; and
obtaining the fourth predicted probability based on the third image set by using the initial image recognition model.

3. The method according to claim 2, wherein the obtaining the first predicted probability based on the first image set by using the initial image recognition model comprises:
obtaining a first predicted value based on the at least one first image by using a fully connected layer comprised in the initial image recognition model; and
performing normalization processing on the first predicted value, to obtain the first predicted probability.

4. The method according to claim 2, further comprising:
generating the second image by:
generating a first perturbed image set according to the at least one second image, the first perturbed image set comprising at least one first perturbed image, the first perturbed image having a correspondence with the second image; and
generating a second perturbed image set according to the at least one second image, the second perturbed image set comprising at least one second perturbed image, the second perturbed image having a correspondence with the second image; and
the obtaining the second predicted probability and the third predicted probability based on the second image set by using the initial image recognition model comprises:
obtaining the second predicted probability based on the at least one second image and the first perturbed image set by using the initial image recognition model; and
obtaining the third predicted probability based on the at least one second image and the second perturbed image set by using the initial image recognition model.

5. The method according to claim 2, wherein the obtaining the fourth predicted probability based on the third image set by using the initial image recognition model comprises:
obtaining a fourth predicted value based on the at least one third image by using a fully connected layer comprised in the initial image recognition model; and
performing normalization processing on the fourth predicted value, to obtain the fourth predicted probability.

6. The method according to claim 1, wherein the determining a target loss function according to the first predicted probability, the second predicted probability, the third predicted probability, and the fourth predicted probability comprises:
calculating the first loss function according to the first predicted probability and labeled information corresponding to the first image set;
calculating the second loss function according to the second predicted probability and the third predicted probability;
calculating the third loss function according to the fourth predicted probability and labeled information corresponding to the third image set;
obtaining an entropy loss function and a regularization loss function; and
obtaining the target loss function according to the first loss function, the second loss function, the third loss function, the entropy loss function, and the regularization loss function.

7. The method according to claim 6, wherein the first loss function is a cross entropy loss function according to the first predicted probability and the labeled information corresponding to the first image set.

8. The method according to claim 6, wherein the second loss function is a consistency loss function or a kullback-leibler (KL) divergence loss function.

9. The method according to claim 6, wherein the third loss function is a cross entropy loss function according to the fourth predicted probability and the labeled information corresponding to the third image set.

10. An electronic device, comprising: a memory, a transceiver, a processor, and a bus system,
the memory being configured to store a program;
the processor being configured to execute the program in the memory, to perform:
obtaining training image sets, the training image sets comprising at least a first image set, a second image set, and a third image set, the first image set comprising at least one first image, the second image set comprising at least one second image and at least one perturbed image, the third image set comprising at least one third image, the first image being a labeled image corresponding to a first task, the second image being an unlabeled image corresponding to the first task, the third image being a labeled image corresponding to a second task, the first task and the second task being different tasks;
obtaining a first predicted probability, a second predicted probability, a third predicted probability, and a fourth predicted probability based on the training image sets by using an initial image recognition model, the first predicted probability being a predicted result outputted based on the first image set, the second predicted probability and the third predicted probability being predicted results outputted based on the second image set, and the fourth predicted probability being a predicted result outputted based on the third image set;
determining a target loss function according to the first predicted probability, the second predicted probability, the third predicted probability, and the fourth predicted probability, the target loss function comprising at least a first loss function determined according to the first predicted probability, a second loss function determined according to the second predicted probability and the third predicted probability, and a third loss function determined according to the fourth predicted probability; and
training the initial image recognition model based on the target loss function, to obtain an image recognition model.

11. The device according to claim 10, wherein the obtaining a first predicted probability, a second predicted probability, a third predicted probability, and a fourth predicted probability based on the training image sets by using an initial image recognition model comprises:
obtaining the first predicted probability based on the first image set by using the initial image recognition model;

obtaining the second predicted probability and the third predicted probability based on the second image set by using the initial image recognition model; and obtaining the fourth predicted probability based on the third image set by using the initial image recognition model.

12. The device according to claim 11, wherein the obtaining the first predicted probability based on the first image set by using the initial image recognition model comprises:

obtaining a first predicted value based on the at least one first image by using a fully connected layer comprised in the initial image recognition model; and performing normalization processing on the first predicted value, to obtain the first predicted probability.

13. The device according to claim 11, wherein the processor is further configured to generate the second image by:

generating a first perturbed image set according to the at least one second image, the first perturbed image set comprising at least one first perturbed image, the first perturbed image having a correspondence with the second image; and generating a second perturbed image set according to the at least one second image, the second perturbed image set comprising at least one second perturbed image, the second perturbed image having a correspondence with the second image; and the obtaining the second predicted probability and the third predicted probability based on the second image set by using the initial image recognition model comprises:

obtaining the second predicted probability based on the at least one second image and the first perturbed image set by using the initial image recognition model; and obtaining the third predicted probability based on the at least one second image and the second perturbed image set by using the initial image recognition model.

14. The device according to claim 11, wherein the obtaining the fourth predicted probability based on the third image set by using the initial image recognition model comprises:

obtaining a fourth predicted value based on the at least one third image by using a fully connected layer comprised in the initial image recognition model; and performing normalization processing on the fourth predicted value, to obtain the fourth predicted probability.

15. The device according to claim 10, wherein the determining a target loss function according to the first predicted probability, the second predicted probability, the third predicted probability, and the fourth predicted probability comprises:

calculating the first loss function according to the first predicted probability and labeled information corresponding to the first image set;

calculating the second loss function according to the second predicted probability and the third predicted probability;

calculating the third loss function according to the fourth predicted probability and labeled information corresponding to the third image set;

obtaining an entropy loss function and a regularization loss function; and obtaining the target loss function according to the first loss function, the second loss function, the third loss function, the entropy loss function, and the regularization loss function.

16. The device according to claim 15, wherein the first loss function is a cross entropy loss function according to the first predicted probability and the labeled information corresponding to the first image set.

17. The device according to claim 15, wherein the second loss function is a consistency loss function or a kullback-leibler (KL) divergence loss function.

18. The device according to claim 15, wherein the third loss function is a cross entropy loss function according to the fourth predicted probability and the labeled information corresponding to the third image set.

19. A non-transitory computer-readable storage medium, comprising instructions, the instructions, when run on a computer, causing the computer to perform:

obtaining training image sets, the training image sets comprising at least a first image set, a second image set, and a third image set, the first image set comprising at least one first image, the second image set comprising at least one second image and at least one perturbed image, the third image set comprising at least one third image, the first image being a labeled image corresponding to a first task, the second image being an unlabeled image corresponding to the first task, the third image being a labeled image corresponding to a second task, the first task and the second task being different tasks;

obtaining a first predicted probability, a second predicted probability, a third predicted probability, and a fourth predicted probability based on the training image sets by using an initial image recognition model, the first predicted probability being a predicted result outputted based on the first image set, the second predicted probability and the third predicted probability being predicted results outputted based on the second image set, and the fourth predicted probability being a predicted result outputted based on the third image set;

determining a target loss function according to the first predicted probability, the second predicted probability, the third predicted probability, and the fourth predicted probability, the target loss function comprising at least a first loss function determined according to the first predicted probability, a second loss function determined according to the second predicted probability and the third predicted probability, and a third loss function determined according to the fourth predicted probability; and training the initial image recognition model based on the target loss function, to obtain an image recognition model.

20. The storage medium according to claim 19, wherein the obtaining a first predicted probability, a second predicted probability, a third predicted probability, and a fourth predicted probability based on the training image sets by using an initial image recognition model comprises:

obtaining the first predicted probability based on the first image set by using the initial image recognition model;

obtaining the second predicted probability and the third predicted probability based on the second image set by using the initial image recognition model; and obtaining the fourth predicted probability based on the third image set by using the initial image recognition model.

\* \* \* \* \*